United States Patent
Gotoh et al.

(10) Patent No.: US 10,307,040 B2
(45) Date of Patent: Jun. 4, 2019

(54) IN-BODY MONITORING CAMERA SYSTEM AND SUPPORT TUBE FOR IN-BODY MONITORING-CAMERA-SYSTEM

(71) Applicant: Sharp Kabushiki Kaisha, Osaka-shi, Osaka (JP)

(72) Inventors: Toshihisa Gotoh, Osaka (JP); Tsuguhisa Inoue, Osaka (JP); Kei Urakawa, Osaka (JP); Hitoshi Aoki, Osaka (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 405 days.

(21) Appl. No.: 14/899,269

(22) PCT Filed: Aug. 7, 2014

(86) PCT No.: PCT/JP2014/070815
§ 371 (c)(1),
(2) Date: Dec. 17, 2015

(87) PCT Pub. No.: WO2015/020124
PCT Pub. Date: Feb. 12, 2015

(65) Prior Publication Data
US 2016/0143510 A1    May 26, 2016

(30) Foreign Application Priority Data

Aug. 8, 2013 (JP) .................. 2013-165593
Mar. 7, 2014 (JP) .................. 2014-045617

(51) Int. Cl.
*A61B 1/00*    (2006.01)
*A61B 1/04*    (2006.01)
(Continued)

(52) U.S. Cl.
CPC .......... *A61B 1/00114* (2013.01); *A61B 1/005* (2013.01); *A61B 1/00105* (2013.01);
(Continued)

(58) Field of Classification Search
CPC ............ A61B 1/00105; A61B 1/00114; A61B 1/00128; A61B 1/00147; A61B 1/005;
(Continued)

(56) References Cited

U.S. PATENT DOCUMENTS 4,323,304 A * 4/1982 Ishii .................. A61B 1/00128
396/17
5,489,256 A * 2/1996 Adair ................. A61B 1/00073
600/123
(Continued)

FOREIGN PATENT DOCUMENTS

| CN | 101322640 A | 12/2008 |
|----|-------------|---------|
| JP | 2005-319086 A | 11/2005 |

(Continued)

OTHER PUBLICATIONS

Aoki et al., "Camera System for Monitoring Inside of Body", U.S. Appl. No. 15/546,291, filed Jul. 26, 2017.
(Continued)

*Primary Examiner* — Timothy J Neal
(74) *Attorney, Agent, or Firm* — Keating & Bennett, LLP

(57) ABSTRACT

The invention is provided with: a camera support tube (13) one end part of which is introduced into a body; a camera unit (11) which is joined to the camera support tube inside the body; a support tube joining portion (14) which joins the camera unit and the camera support tube; a camera-side cable (12) which is connected to the camera unit and led out to an outside of the body through the camera support tube;
(Continued)

and a control system that is provided outside the body is connected to the camera-side cable, and includes at least a display (18).

21 Claims, 22 Drawing Sheets

(51) Int. Cl.
- *A61B 1/05* (2006.01)
- *A61B 1/313* (2006.01)
- *A61B 90/00* (2016.01)
- *A61B 1/005* (2006.01)
- *A61B 17/00* (2006.01)

(52) U.S. Cl.
CPC ...... *A61B 1/00128* (2013.01); *A61B 1/00147* (2013.01); *A61B 1/041* (2013.01); *A61B 1/053* (2013.01); *A61B 1/3132* (2013.01); *A61B 90/361* (2016.02); *A61B 2017/00477* (2013.01)

(58) Field of Classification Search
CPC ....... A61B 1/041; A61B 1/053; A61B 1/3132; A61B 2017/00477; A61B 90/361
See application file for complete search history.

(56) References Cited

U.S. PATENT DOCUMENTS

| | | | | |
|---|---|---|---|---|
| 5,630,782 | A * | 5/1997 | Adair | A61B 1/00073 600/123 |
| 5,643,175 | A * | 7/1997 | Adair | A61B 1/00073 600/123 |
| 5,754,896 | A * | 5/1998 | Aoki | G03B 3/00 396/144 |
| 2003/0114731 | A1 | 6/2003 | Cadeddu et al. | |
| 2003/0120130 | A1* | 6/2003 | Glukhovsky | A61B 1/00181 600/109 |
| 2004/0133076 | A1* | 7/2004 | Kobayashi | A61B 1/00016 600/175 |
| 2005/0165272 | A1* | 7/2005 | Okada | A61B 1/0008 600/114 |
| 2006/0074307 | A1 | 4/2006 | Igarashi et al. | |
| 2006/0189846 | A1* | 8/2006 | Huang | A61B 1/041 600/160 |
| 2006/0253126 | A1* | 11/2006 | Bjerken | A61B 17/0469 606/139 |
| 2007/0161855 | A1* | 7/2007 | Mikkaichi | A61B 1/0005 600/113 |
| 2007/0255100 | A1* | 11/2007 | Barlow | A61B 1/0005 600/114 |
| 2008/0015413 | A1 | 1/2008 | Barlow et al. | |
| 2008/0255458 | A1* | 10/2008 | Dunki-Jacobs | A61B 5/0071 600/476 |
| 2008/0294002 | A1* | 11/2008 | Xie | A61B 1/043 600/109 |
| 2008/0309758 | A1 | 12/2008 | Karasawa et al. | |
| 2008/0312499 | A1* | 12/2008 | Handa | A61B 1/0005 600/109 |
| 2008/0312500 | A1* | 12/2008 | Asada | A61B 1/0005 600/109 |
| 2009/0306470 | A1* | 12/2009 | Karasawa | A61B 1/04 600/103 |
| 2009/0322864 | A1* | 12/2009 | Karasawa | A61B 1/00147 348/65 |
| 2010/0036199 | A1* | 2/2010 | Karasawa | A61B 1/00085 600/109 |
| 2010/0076259 | A1* | 3/2010 | Asada | A61B 1/00096 600/102 |
| 2010/0249503 | A1* | 9/2010 | Yazawa | A61B 1/00091 600/109 |
| 2011/0046440 | A1* | 2/2011 | Asada | A61B 1/00147 600/104 |
| 2011/0046445 | A1* | 2/2011 | Asada | A61B 1/041 600/158 |
| 2011/0254938 | A1* | 10/2011 | Asada | A61B 1/041 348/76 |
| 2012/0016197 | A1* | 1/2012 | Turnbull | A61B 1/00105 600/109 |
| 2012/0050511 | A1* | 3/2012 | Takahashi | A61B 1/00114 348/65 |
| 2012/0123463 | A1* | 5/2012 | Jacobs | A61B 17/00234 606/191 |
| 2012/0232345 | A1* | 9/2012 | Levy | A61B 1/0014 600/112 |
| 2014/0243597 | A1* | 8/2014 | Weisenburgh, II | A61B 1/00158 600/112 |
| 2014/0284751 | A1* | 9/2014 | Kamei | H01L 27/14618 257/443 |
| 2015/0148599 | A1* | 5/2015 | Wilson | A61B 1/00124 600/109 |

FOREIGN PATENT DOCUMENTS

| | | |
|---|---|---|
| JP | 2010-012222 A | 1/2010 |
| JP | 4472727 B2 | 6/2010 |
| JP | 4599474 B1 | 12/2010 |
| JP | 2012-239519 A | 12/2012 |
| WO | 2007/078003 A1 | 7/2007 |
| WO | 2007/097393 A1 | 8/2007 |
| WO | 2012/026156 A1 | 3/2012 |

OTHER PUBLICATIONS

Inoue et al., "In-Vivo Monitoring Camera System, and Support Tube for In-Vivo Monitoring Camera System", U.S. Appl. No. 15/031,777, filed Apr. 25, 2016.

Urakawa et al., "Intracorporeal-Monitoring Camera System, Support Tube for Intracorporeal-Monitoring Camera System, and Cable Holder for Intracorporeal-Monitoring Camera System", U.S. Appl. No. 14/917,064, filed Mar. 1, 2016.

Urakawa et al., "Camera System for Monitoring Inside of Body, Accessory for Support Tube of Camera System for Monitoring Inside of Body, Fixing Tool for Camera System for Monitoring Inside of Body, and Method for Installing Camera System for Monitoring Inside of Body", U.S. Appl. No. 15/031,816, filed Apr. 25, 2016.

Aoki et al., "Camera System for Monitoring Inside of Body and Auxiliary Device and Method for Installing Imaging Apparatus for Monitoring Inside of Body", U.S. Appl. No. 15/111,514, filed Jul. 14, 2016.

Aoki et al., "In-Body Monitoring Camera System and Camera Unit", U.S. Appl. No. 15/129,044, filed Sep. 26, 2016.

Aoki et al., "Camera System for Monitoring Inside of Body and Auxiliary Tool Set", U.S. Appl. No. 15/112,726, filed Jul. 20, 2016.

* cited by examiner

53: SCREW GROOVE
55: SCREW THREAD
52: CAMERA SUPPORT TUBE
214: SUPPORT TUBE JOINING PORTION

IN-BODY MONITORING CAMERA SYSTEM AND SUPPORT TUBE FOR IN-BODY MONITORING-CAMERA-SYSTEM

TECHNICAL FIELD

The present invention relates to an in-body monitoring camera system which includes an imaging portion capable of being introduced into a body.

BACKGROUND ART

Endoscopic surgery is minimally invasive surgery for performing examination or therapeutic treatment without performing a laparotomy for a patient. For the endoscopic surgery, a surgical instrument such as forceps and an endoscope are introduced separately into a body cavity of a patient. A surgeon captures an image of a tip part of the surgical instrument, which has been introduced into the body cavity, within an observation field of the endoscope and performs a work for the treatment while observing, with the endoscope, a state of a site where the surgical instrument is adapted for treating the patient. For the endoscopic surgery, the surgical instrument and the endoscope are introduced into the body cavity through a pipe (called a trocar) that is placed through the abdominal wall of the patient.

The surgeon brings the endoscope in close to an organ and enlarges the image of the organ when performing an incision or a suture of the organ, so that a visual field becomes extremely narrow. Accordingly, demanded is an apparatus with which states in a region outside a working region (motion of the surgical instrument outside the working region, a bleeding place, a residue such as gauze, and the like) are able to be widely grasped.

In response to such a demand, PTL 1 discloses an apparatus which directly inserts a connector electrode having a needle shape into an abdominal wall and joins the connector electrode and a camera inside a body.

Moreover, PTL 2 discloses an apparatus which inserts a camera unit and a communication cable joined thereto from a trocar and leads out a needle and the communication cable to an outside of a body from a hole in an abdominal wall, in a state where an end part of the communication cable is hooked on the needle which is inserted from the hole in the abdominal wall, to fix the communication cable.

CITATION LIST

Patent Literature

PTL 1: Japanese Patent Publication No. 4472727 (issued on Jun. 2, 2010)
PTL 2: Japanese Patent Publication No. 4599474 (issued on December 15)

SUMMARY OF INVENTION

Technical Problem

In PTL 1, since the connector electrode having the needle shape is directly inserted into the abdominal wall and the connector electrode and the camera are joined inside the body, there is a risk that electrical connection failure is caused due to foreign matter mixed in a joining portion of the connector electrode and the camera.

In PTL 2, the communication cable is led out to the outside of the body to be fixed, but because of a property of the communication cable, it is difficult to obtain joining strength of the communication cable and the camera unit, and it is also difficult to change an orientation of the camera unit from outside the body.

The present invention proposes an in-body monitoring camera system which is highly reliable and easy to use.

Solution to Problem

The present in-body monitoring camera system includes: a support tube one end part of which is introduced into a body; an imaging portion which is joined to the support tube inside the body; a joining portion which joins the imaging portion and the support tube; a first cable which is connected to the imaging portion and led out to an outside of the body through the support tube; and a control system which exists outside the body, is connected to the first cable, and includes at least a display apparatus.

Advantageous Effects of Invention

In one aspect of the present in-body monitoring camera system, it is possible to join the imaging portion to the support tube inside the body in a state where the cable is inserted into the support tube. Accordingly, supporting force for the imaging portion is increased, and connection failure of the imaging portion and the cable is less likely to be caused, so that high reliability is achieved. Moreover, a surgeon is able to change an orientation of the imaging portion inside the body via the support tube, so that high usability is achieved.

DESCRIPTION OF EMBODIMENTS

One embodiment of the invention will be described based on FIG. 1 to FIG. 22 as follows. Note that, for convenience of description, the same reference signs are assigned to members having the same functions as those of members indicated in each embodiment, and description thereof will be omitted appropriately. Moreover, shapes nor dimensions, such as a length, a size, and a width, of configurations illustrated in each figure does not represent actual shapes nor dimensions, and are appropriately changed for clarification and simplification of figures.

Embodiment 1

(Configuration of in-Body Monitoring Camera System)

Figure 1:
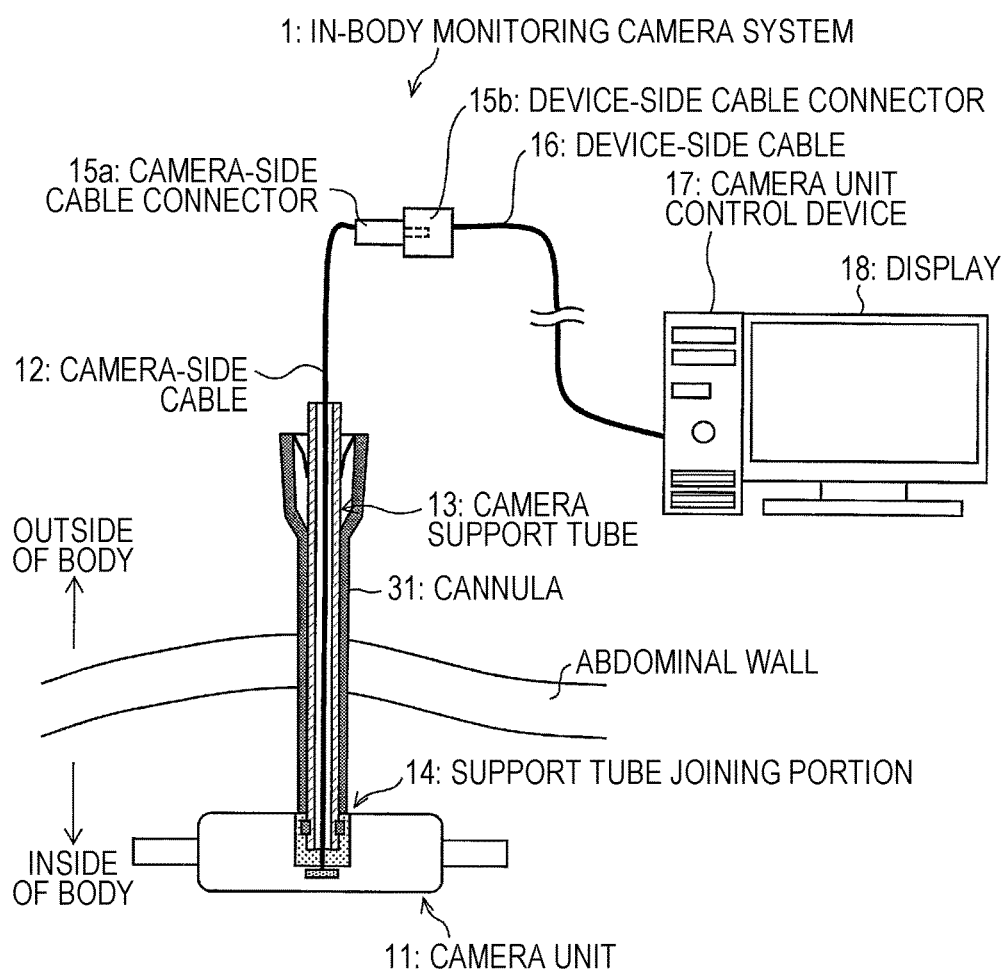
FIG. 1 is a schematic view illustrating a configuration of an in-body monitoring camera system according to Embodiment 1.

FIG. 1 is a schematic view illustrating a configuration of an in-body monitoring camera system of Embodiment 1. As illustrated in FIG. 1, an in-body monitoring camera system 1 is provided with: an imaging apparatus including a camera unit 11 (imaging portion), and a camera-side cable 12 (first cable) which is connected thereto and a camera-side cable connector 15a (first connector); a camera support tube 13 (support tube); a device-side cable connector 15b (second connector); a device-side cable 16 (second cable); and a control system including a camera unit control device 17 and a display 18 (display apparatus). Note that, the cable connectors are hereinafter referred to as a "cable connector 15" collectively in some cases.

One end part of the camera support tube 13 is introduced into a body through an inner part of a cannula 31 (holding tube) puncturing an abdominal wall. The camera unit 11 which performs in-body photographing is introduced into the body through a tube-shaped member called a trocar. Then, in a state where the camera-side cable 12 is inserted into an inner part of the camera support tube 13, the one end part (intracorporeal side) of the camera support tube 13 and the camera unit 11 inside the body are joined by the support tube joining portion 14 (joining portion).

The camera unit 11 is connected to the camera unit control device 17 via the camera-side cable 12, the camera-side cable connector 15a, the device-side cable connector 15b, and the device-side cable 16, a video photographed by the camera unit 11 is transmitted to the camera unit control device 17, and a control signal from the camera unit control device 17 is transmitted to the camera unit 11. Specifically, the camera-side cable 12 and the device-side cable 16 are connected by fitting the camera-side cable connector 15a provided in an end part of the camera-side cable 12, which is in a side opposite to a side connected to the camera unit 11, to the device-side cable connector 15b provided in an end part of the device-side cable 16, which is in a side opposite to a side connected to the camera unit control device 17. For example, as illustrated in FIG. 1, when a pin part of the male camera-side cable connector 15a is inserted into the female device-side cable connector 15b, the both cable connectors are fit to each other. Thereby, the camera unit 11 and the camera unit control device 17 are connected. Note that, male and female may be reversed, and it may be configured such that the female camera-side cable connector 15a and the male device-side cable connector 15b are fit to each other.

Note that, when connecting the camera unit 11 and the camera support tube 13, the camera-side cable connector 15a and the camera-side cable 12 are led out to an outside of a body from an inside of the body through the camera support tube 13, which will be described below in detail. Therefore, an outer diameter of the camera-side cable connector 15a is smaller than an outer diameter of the camera support tube 13. Thus, by reducing the outer diameter of the camera-side cable connector 15a, it is possible to reduce the outer diameter of the camera support tube 13. Thereby, an exceptional effect of reducing invasiveness is realized. That is, it is desired that the outer diameter of the camera-side cable connector 15a is reduced as much as possible. For example, as illustrated in FIG. 1, it is desired that the outer diameter of the camera-side cable connector 15a is equal to or less than an outer diameter of the device-side cable connector 15b.

Note that, in FIG. 1, the outer diameter of the camera-side cable connector 15a is illustrated so as to be larger than an actual outer diameter in order to make the figure easy to see. As described above, the outer diameter of the camera-side cable connector 15a is actually smaller than the outer diameter of the camera support tube 13. In addition, in FIG. 1, one pin part is illustrated for simplification. The camera-side cable connector 15a is normally configured to have pins of the number according to the number of electric wires to be used in a cable. This is similar also in other figures in which the camera support tube 13 and the camera-side cable connector 15a are illustrated.

Since a wired system is adopted for transmission from the camera unit 11 to the camera unit control device 17, it is possible to increase transmission speed and transmit/receive a signal stably, thus making it possible to obtain a high-resolution image. Moreover, compared to a wireless system, it is possible to perform communication with low electric power, and miniaturization of the camera unit 11 is able to be attained by supplying a power source from outside. Accordingly, with the miniaturization, it is possible to make a wound, which is made when the camera unit 11 is introduced into the body, small, so that an exceptional effect of reducing invasiveness is realized.

The camera unit control device 17 causes the display 18 to display a video transmitted from the camera unit 11 and transmits a control signal to the camera unit 11. Note that, the camera unit control device 17 and the display 18 may be configured integrally or separately.

(Configuration of Imaging Apparatus)

FIG. 2(a) is a schematic sectional view of the camera unit of Embodiment 1 and FIG. 2(b) is a top view thereof. As illustrated in FIGS. 2(a) and (b), the camera unit 11 is provided with a circuit board 19, a solid-state image sensor 25, a control circuit 28, and an illuminating apparatus 27, which are connected to the circuit board 19, and a lens 26 in a camera housing 21. In a top surface of the camera housing 21, the recess-shaped support tube joining portion 14 is provided. The support tube joining portion 14 has a hollow structure whose opening is circular and is provided with locking pawls 23 (protrusions) in an inner wall thereof. Further, gripping portions 22 respectively project from both of facing side surfaces of the camera housing 21. By using forceps, the gripping portions 22 are gripped when the camera unit 11 is introduced into a body, and gripped so that a top surface of the camera unit 11 (a surface in which the support tube joining portion 14 is provided) faces the end part of the camera support tube 13 when the camera unit 11 and the camera support tube 13 are joined, for example.

The camera-side cable 12 is connected to the circuit board 19 and led out of the camera unit 11 so as to pass through an inner part of the support tube joining portion 14. A part in which the circuit board 19 and the camera-side cable 12 are connected is sealed with resin or the like. Furthermore, in a part of the inner part of the support tube joining portion 14, from which the camera-side cable 12 is led out (a bottom part of the recess-shaped support tube joining portion 14), the camera-side cable 12 is adhesively fixed to the inner part of the support tube joining portion 14 (sealed and fixed, for example, with an adhesive agent or an O-ring), which provides a configuration in which water intrusion, mixing of foreign matter, and the like are not caused from the part (into the camera unit 11). For being introduced into a body cavity through a trocar, the camera-side cable 12 is formed of a flexible material.

Figure 2:
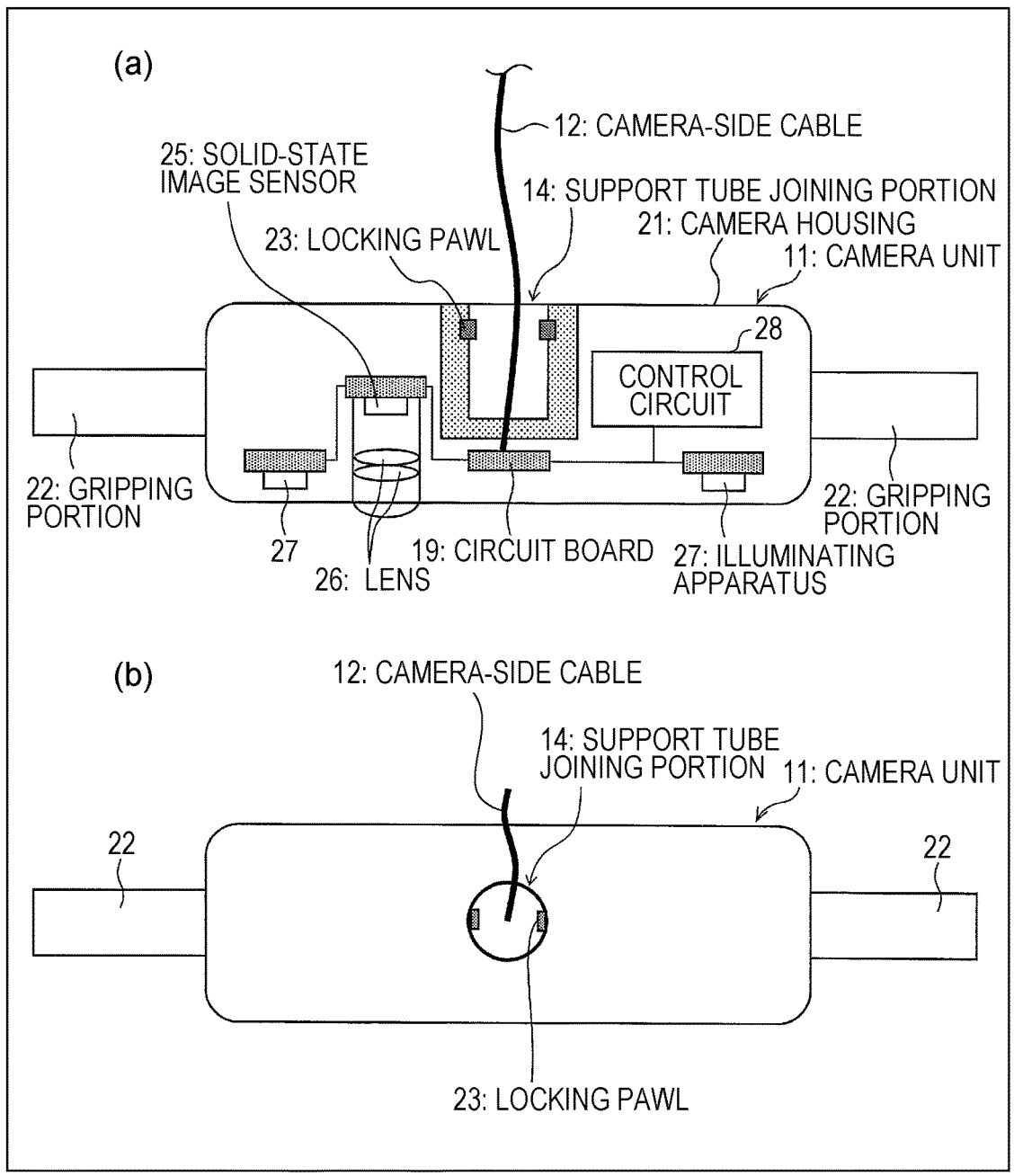
FIG. 2(a) is a schematic sectional view of a camera unit according to Embodiment 1, and (b) is a top view thereof.

The solid-state image sensor 25 is a CCD, a CMOS image sensor, or the like, and the illuminating apparatus 27 illuminates inside the body to thereby make the video photographed by the camera unit 11 clear. It is preferable that the illuminating apparatus 27 has a small size, and, for example, an LED or the like is able to be used suitably. Note that, as illustrated in FIG. 2, a plurality of illumination apparatuses 27 may be provided in the camera unit 11.

A part in the camera housing 21 of the camera unit 11, in which the lens 26 and the illuminating apparatus 27 are arranged, is formed of a transparent material, but it is desirable that the other region is formed of a blue or green material which is conspicuous in the body. Moreover, it is further desirable that a film on a surface of the camera-side cable 12 is formed of a blue or green material. Furthermore, it is desirable that the camera-side cable connector 15a is also formed of a material which is colored similarly. In this manner, by using blue or green which is complementary to a color inside a body, which is red or yellow, it is possible to facilitate visual recognition at a time of an in-body installation work or collection work, which will be described below. For example, even when the camera unit 11 is dropped into the body by mistake and hidden by an organ, as illustrated in FIG. 21(a), the camera-side cable 12 is long compared to the camera unit 11 and thus able to be seen in a place, which allows visual recognition, in many cases, so that it is easy to be found immediately. Thus, when the camera-side cable 12 is in blue or green, exceptional effects that a time for the installation work of the camera unit 11 is able to be shortened and safety is enhanced are realized.

FIGS. 21(b) and (c) illustrate an example of a state where the camera-side cable 12, the camera-side cable connector 15a, and a part other than the part where the lens 26 and the illuminating apparatus 27 are arranged in the camera housing 21 are colored. As illustrated in FIGS. 21(b) and (c), the part other than the part where the lens 26 and the illuminating apparatus 27, which need to be formed of a transparent material, are arranged is colored blue or green which is easy to be visually recognized in a body (in FIGS. 21(b) and (c), the colored part is indicated with a rhombic pattern). Note that, in FIGS. 21(b) and (c), an example that the whole of the material described above is entirely colored is illustrated, but not the whole but a part of the camera-side cable 12, the camera-side cable connector 15a, and the part other than the part where the lens 26 and the illuminating apparatus 27 are arranged in the camera housing 21 may be colored.

In addition to the blue or green material used for coloring as above, as a material to be used for surfaces of the camera-side cable 12, the camera-side cable connector 15a, and the part other than the part where the lens 26 and the illuminating apparatus 27 are arranged in the camera housing 21, a light accumulating material or a reflective material, which is easy to be visually recognized, may be used. This makes it possible to immediately find them when being behind an organ and therefore difficult to be visually recognized or in an edge of a visual field, to which illuminating light is difficult to reach, so that it is particularly effective.

(Configurations of Camera Support Tube and Cannula)

Figure 3:
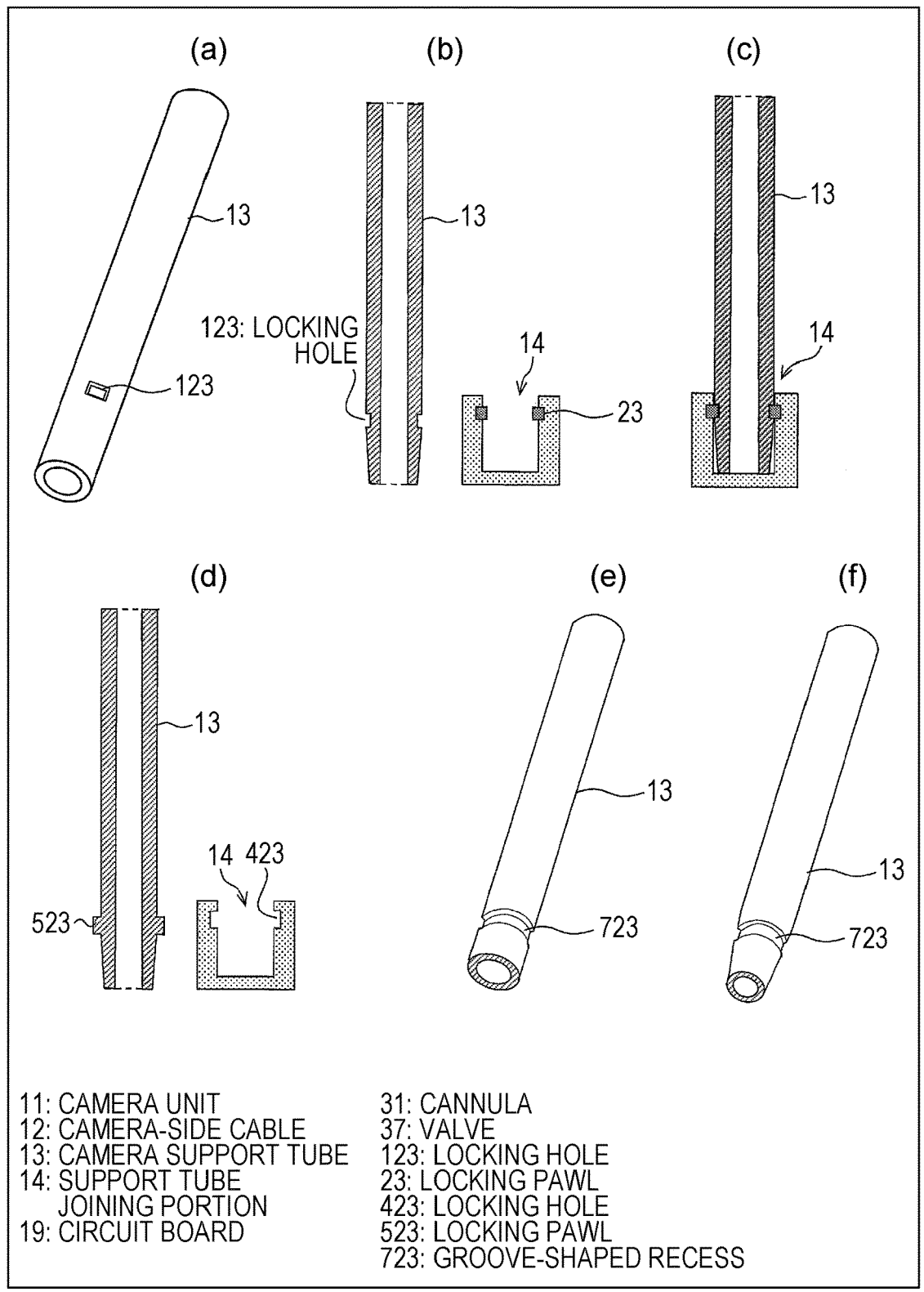
FIG. 3(a) is a perspective view of a camera support tube of FIG. 1, (b) is a sectional view of the camera support tube and a support tube joining portion of FIG. 1, and (c) is a sectional view illustrating a state where the camera support tube and the support tube joining portion of FIG. 1 are joined. (d) is a sectional view illustrating a modified example of the camera support tube and the support tube joining portion, and (e) and (f) are perspective views illustrating modified examples of the camera support tube of (a).
Figure 4:
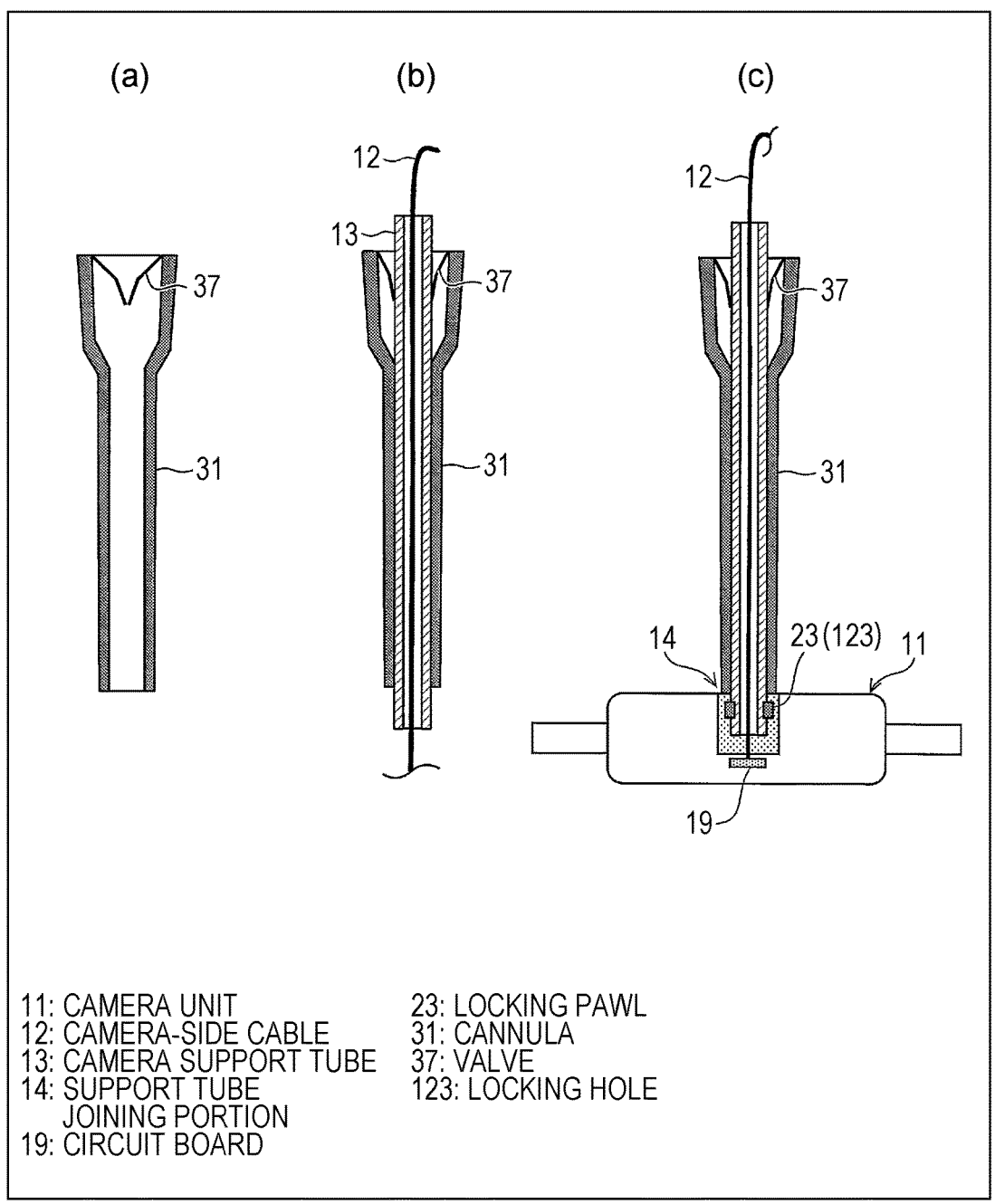
FIG. 4(a) is a sectional view illustrating a configuration of a cannula, (b) is a sectional view illustrating a state where the camera support tube of FIG. 3 is inserted into the cannula of FIGS. 4(a), and (c) is a sectional view illustrating a state where the camera support tube inserted into the cannula and the camera unit of FIG. 2 are joined.
Figure 5:
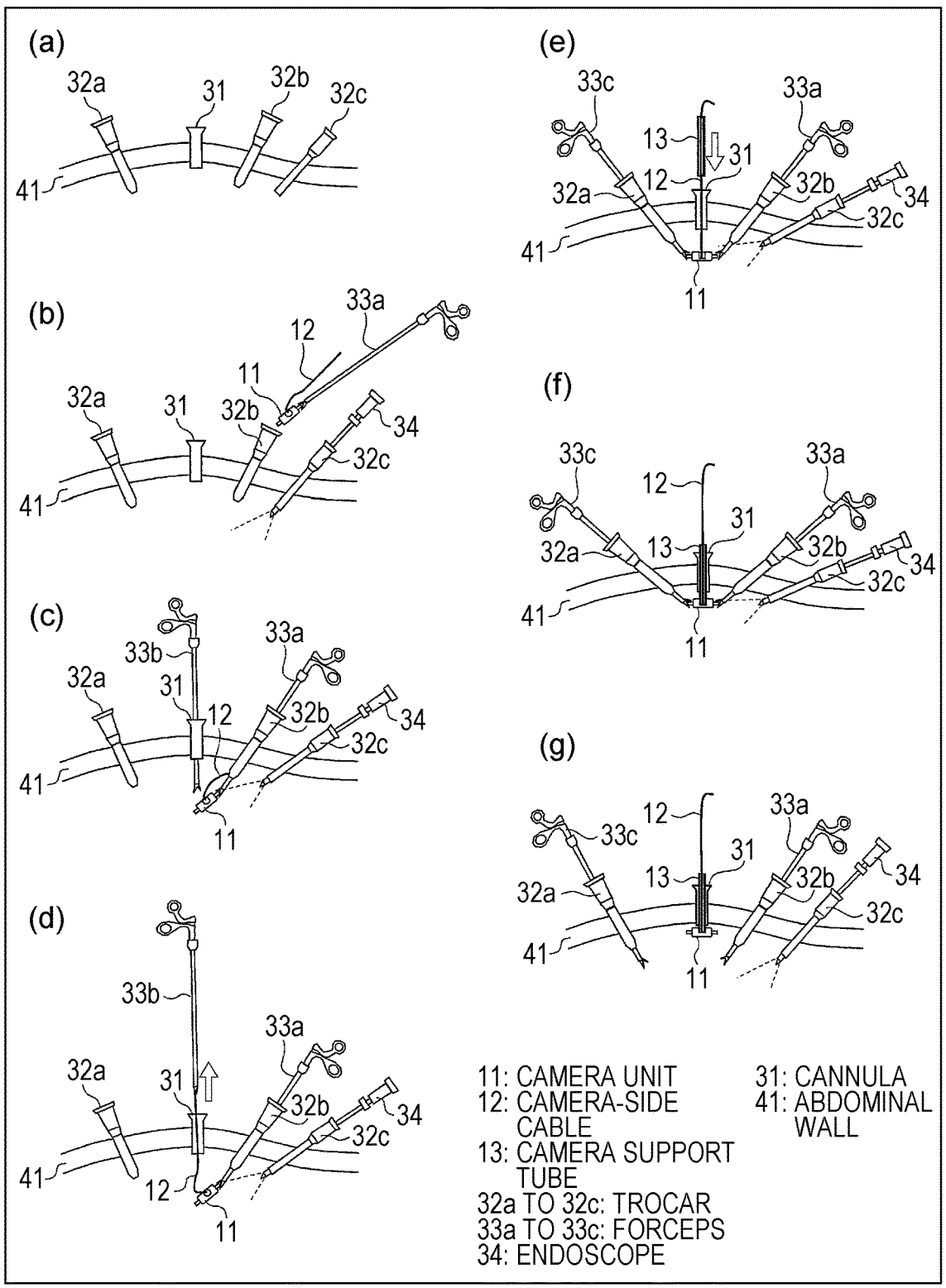
FIGS. 5(a) to (g) are schematic views illustrating a method of installing the camera unit in a body in Embodiment 1.

FIG. 3 illustrates schematic configurations of the camera support tube and the support tube joining portion. FIG. 3(a) is a perspective view of the camera support tube. As illustrated in FIG. 3(a), the camera support tube 13 is a cylindrical tube and has locking holes 123 (recesses) in an end part on a side which is introduced into a body. From a viewpoint of joining strength with the camera unit 11, the camera support tube 13 is formed of a hard material. Because of the cylindrical shape, the camera support tube 13 is resistant to physical impacts, and easy to be combined with a common cannula which is similarly a cylindrical tube. Note that, as the camera support tube, a common tubular tool such as a trocar or a cannula may be directly used. Moreover, a puncturing tool a tip end of which is sharpened or which has a shape subjected to oblique cut like an injection needle may be used.

FIG. 3(b) is a sectional view of the camera support tube and the support tube joining portion, and FIG. 3(c) is a sectional view illustrating a state where the camera support tube is inserted into the support tube joining portion. Since a part of the camera support tube 13, which is in a tip side further than the locking holes 123, has a tapered shape as illustrated in FIGS. 3(b) and (c), the tip end (intracorporeal side) of the camera support tube 13 is not hooked on the locking pawls 23 of the support tube joining portion 14, and when the camera support tube 13 is thrust until the tip end reaches deep in the support tube joining portion 14, the locking pawls 23 are to be fit to the locking holes 123. Note that, the configuration of the camera support tube 13 is not limited to the above. Both end parts of the camera support tube 13 may have the same thickness. A shape of the tip end which is subjected to oblique cut like an injection needle for easy puncture may be used.

The locking holes 123 may be provided in a part (at least two sites) of an outer periphery of the camera support tube 13 as illustrated in FIG. 2(b) and FIG. 3(a), or a groove-shaped recess 723 which is formed around an outside surface thereof may be provided in the end part of the camera support tube 13 and a ridge-like protrusion which is formed around along an inside surface of the opposing support tube joining portion 14 may be provided, as illustrated in FIG. 3(e). This is more desirable since it is not necessary to perform an operation of matching positions of the locking holes 123 and the locking pawls 23 when inserting the camera support tube 13, and it becomes easier to join the both.

Moreover, in the case of forming a tip end part of the camera support tube 13 in the tapered shape in order to facilitate the insertion thereof, the tapered shape is able to be obtained by reducing thickness of the camera support tube 13, as illustrated in FIG. 3(f). At this time, by setting an inner diameter of the camera support tube 13 to be fixed and changing only the outer diameter (setting an external form to be smaller as being close to the tip end), when a tool is inserted into the camera support tube, it is not likely to happen, for example, that the tool is hooked midway (at a narrowed site) and becomes unable to be pulled out, so that it is more desirable.

Note that, as illustrated in FIG. 3(d), locking pawls 523 may be provided in the camera support tube 13, and locking holes 423 may be provided in the support tube joining portion 14. In this case as well, instead of the locking pawls 523 and the locking holes 423, a ridge-like protrusion which is formed around the outside surface may be provided in the end part of the camera support tube 13 and a groove-shaped recess which is formed around along the inside surface of the opposing support tube joining portion 14 may be provided.

Each of the camera support tube 13 and the support tube joining portion 14 may be formed of a plurality of materials. For example, the locking pawls 23 and the locking pawls 523, which are described above, may be formed of an elastic material such as resin. That is, at least one of a recess of the camera support tube 13 and a protrusion of the support tube joining portion 14 may be formed of the elastic material such as resin, and the other may be formed of a hard material such as metal.

With such formation, when passing through sites, in which the locking pawls 23 (elastic material) of the support tube joining portion 14 are arranged and which are narrowed to some extent, the elastic material deforms, and, after passing through, returns to the original shape with elastic force to be fit firmly, so that joining strength is increased. Without limitation to this example, an elastic material may be used for at least one of the recess and the protrusion of the camera support tube 13 and the support tube joining portion 14.

Accordingly, it is possible for a surgeon, who performs an operation, to sense response of fitting since a fitting impact is transmitted to his/her hand, and to recognize that fitting has been performed successfully, so that there is an advantage that excessive force is not to be applied continuously.

Further, when a plurality of materials which have different properties are used for the formation such that side surfaces of the camera support tube 13 and the support tube joining portion 14 are formed of a material, which has high thermal conductivity, for enhancing a heat radiation property from the camera unit 11, the elastic material is used only for the protrusion part of the support tube joining portion 14 for enhancing the joining strength, and a function of sensing response of fitting is added, it is possible to achieve a plurality of properties, which are required, such as a joining property and the heat radiation property.

Note that, regardless of the formation example of the above-described example, the combination of these materials may be reversed. That is, when description is given with an example of FIG. 3(b), the locking pawls 23 may be formed of a hard material such as metal and a part including the locking holes 123 may be formed of an elastic material such as resin.

Though description has been given for various examples as above, it is needless to say that materials for forming the camera support tube 13 and the support tube joining portion 14 as such are able to be used in a plurality of combinations similarly even in other embodiments.

(Insertion into Cannula and Joining to Camera Unit of Camera Support Tube)

FIG. 4(a) is a sectional view of the cannula. As illustrated in FIG. 4(a), the cannula 31 is a tubular device, and has a configuration that one end part thereof (extracorporeal side) is thicker than the other end part (intracorporeal side), and a valve 37 having restorability is included inside the one end part (extracorporeal side). The valve 37 has, in the middle part thereof, a configuration of a valve which is spread out when external force is applied in a direction from the thicker end part (extracorporeal side) to the thinner end part (intracorporeal side).

For the case of joining the camera unit 11 to the camera support tube 13 inside a body, first, a thinner end part of the camera support tube 13 is pressed against the thicker end part (extracorporeal side) of the cannula 31 in a state where the camera-side cable 12 is inserted into the inner part of the camera support tube 13, and the camera support tube 13 is then inserted into the cannula 31 until the thinner end part of the camera support tube 13 is exposed from the cannula 31, as illustrated in FIG. 4(b). At this time, the valve 37 is spread out by the camera support tube 13 and tightly fastens the camera support tube 13 with the restorability, resulting that the camera support tube 13 is fixed to the cannula 31. Note that, a thicker end part (extracorporeal side) of the camera support tube 13 is also caused to be exposed from the cannula 31. Next, as illustrated in FIG. 4(c), by inserting the thinner end part (intracorporeal side) of the camera support tube 13 into the recess-shaped support tube joining portion 14 by using the camera-side cable 12 as a guide, the locking pawls 23 are fit to the locking holes 123, and the camera unit 11 and the camera support tube 13 are joined with high mechanical strength. Note that, any shapes may be applicable to the locking pawls 23 and the locking holes 123 as long as being capable of fitting to each other, and an O-ring or the like may be also used instead of the locking pawls 23.

Note that, it is desirable that strength of fitting the camera support tube 13 and the support tube joining portion 14 is set to be smaller than adhesive strength of an adhesively fixing part where the camera-side cable 12 and the camera unit 11 are adhesively fixed. This is because, since it is necessary to insert the camera support tube 13 while holding the cable with tension for support at a time of insertion into the support tube joining portion 14 of the camera unit 11, if the fitting strength of the camera support tube 13 and the support tube joining portion 14 is larger than the adhesive strength of the adhesively fixing part, there is a possibility that the adhesively fixing part is broken.

Specifically, it is desirable that the strength of fitting the camera support tube 13 and the support tube joining portion 14 is set to, for example, 30 N (newton) or less, which is smaller than the adhesive strength of the adhesively fixing part. Furthermore, as an optimal range, it is desirable to perform setting within a range from 3 N to 6 N. By setting within this range, it is possible to perform fitting without applying excessively large force at a time of fitting, and an impact of fitting of the camera support tube 13 is transmitted to a hand, so that an exceptional effect that installation is able to be performed safely without applying excessive force continuously is realized.

(Method of Using and Effect of in-Body Monitoring Camera System in Embodiment 1)

Figure 6:
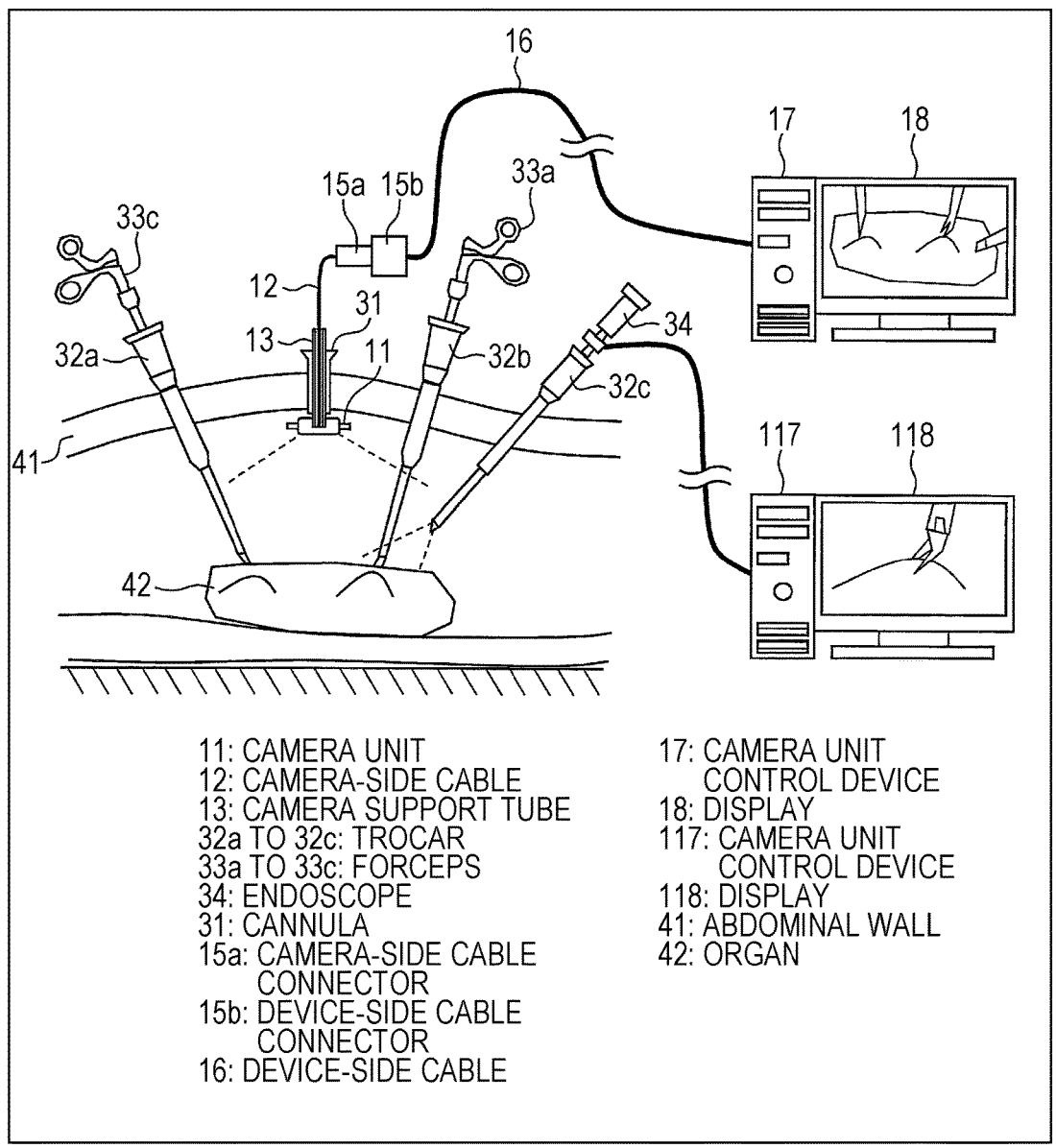
FIG. 6 is a schematic view illustrating a method of using the camera unit in Embodiment 1.
Figure 7:
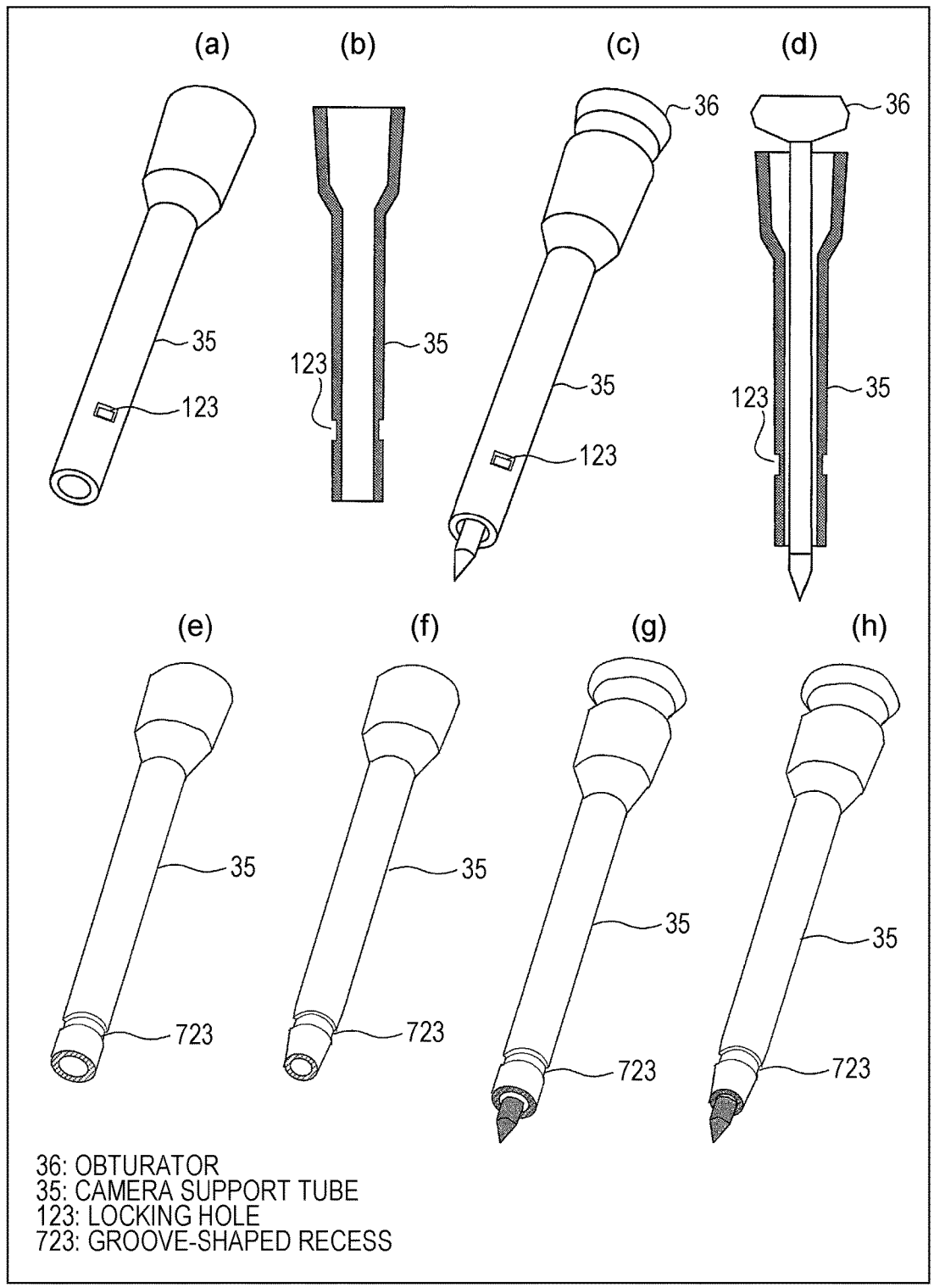
FIG. 7(a) is a perspective view of a camera support tube of Embodiment 2, (b) is a sectional view of the camera support tube of (a), (c) is a perspective view when the camera support tube of (a) is combined with an obturator, (d) is a sectional view of (c), (e) and (f) are perspective views illustrating modified examples of the camera support tube of (a), and (g) and (h) are perspective views illustrating modified examples of the combination of the camera support tube and the obturator of (c).
Figure 8:
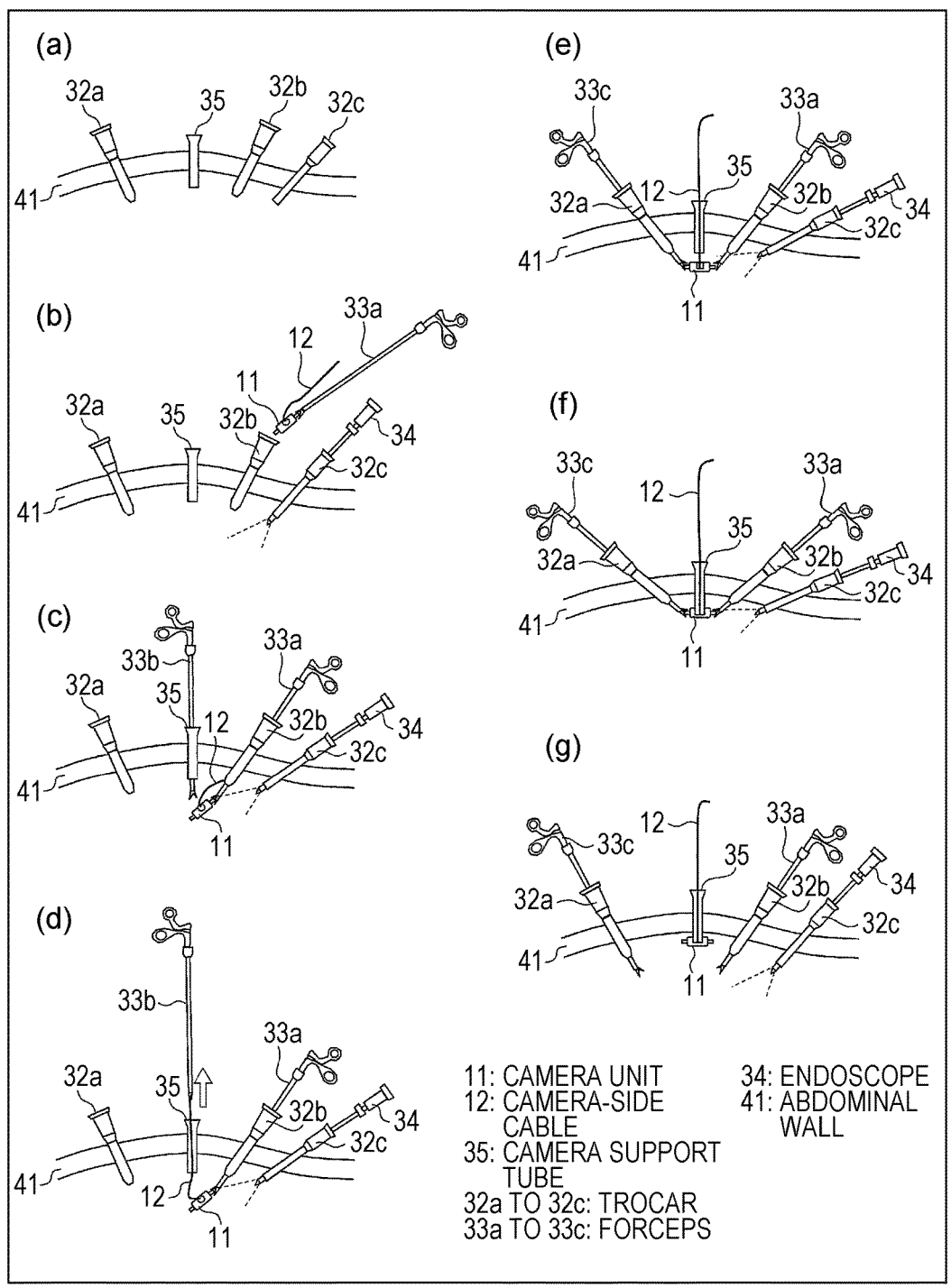
FIGS. 8 (a) to (g) are schematic views illustrating a method of installing the camera unit in a body in Embodiment 2.

FIGS. 5(a) to (g) are schematic views illustrating a method of installing the camera unit in a body in Embodiment 1, and FIG. 6 is a schematic view illustrating a situation of using the in-body monitoring camera system in Embodiment 1.

As illustrated in FIG. 5(a), first, a surgeon incises a body wall 41 for holes (ports) through which forceps or an endoscope is inserted into a body cavity, and inserts trocars 32a to 32c into the ports. Further, in order to install the camera unit 11 in the body cavity, a port is incised at a position in the body wall 41, from which an entire of an organ including an affected part is able to be seen, and the cannula 31 is inserted. Specifically, when a needle-shaped obturator punctures the port in a state where the obturator is inserted into the cannula 31, the cannula 31 is inserted into the body wall 41. In order to realize low invasiveness, it is preferable that the cannula 31 has a short diameter. Specifically, it is preferable that the cannula 31 has a diameter of 3 mm or less. Note that, after at least one of the trocars 32a to 32c and the cannula 31 is inserted, the surgeon sends gas into the body through the trocar to distend the body cavity in advance for securing a space into which a tool is inserted.

Next, as illustrated in FIG. 5(b), the surgeon inserts the endoscope 34 into the body cavity through the trocar 32c, and inserts the camera unit 11 gripped with forceps 33a into the body cavity through the trocar 32b while observing inside the body by using the endoscope 34.

Then, as illustrated in FIG. 5(c), the surgeon operates the forceps 33a to move the camera unit 11 to a vicinity of the cannula 31 and inserts forceps 33b into the body cavity through the cannula 31.

Next, as illustrated in FIG. 5(d), the surgeon pulls out the forceps 33b from the cannula 31 in a state where the camera-side cable 12 is held by the forceps 33b, and thereby leads out the camera-side cable 12 to the outside of the body. At this time, the camera unit 11 (the gripping portion 22 thereof) is in a state of being gripped by the forceps 33a.

Subsequently, as illustrated in FIG. 5(e), the surgeon inserts the forceps 33c into the body cavity through the trocar 32a, and then grips the gripping portions 22 in the both side surfaces of the camera unit 11 by the two forceps 33a and 33c so that the support tube joining portion 14 of the camera unit 11 and an opening of the cannula 31 are in parallel and proximate to each other, inserts the camera-side cable 12, which has been led out to the outside of the body, into the inner part of the camera support tube 13, and inserts the camera support tube 13 into the cannula 31.

Next, as illustrated in FIG. 5(f), by using the camera-side cable 12 as a guide, the surgeon inserts the end part of the camera support tube 13, which is exposed from the cannula 31, into the support tube joining portion 14 of the camera unit 11 and joins the camera support tube 13 and the camera unit 11.

When inserting the camera support tube 13 into the support tube joining portion 14, since force required for fitting the camera support tube 13 and the support tube joining portion 14 (for example, 3 N to 6 N) is set to be substantially smaller than the adhesive strength of the adhesively fixing part of the camera-side cable 12 and the camera unit 11 (for example, 30 N or more), it is possible to safely insert the camera support tube 13 to be fit by using the cable as the guide with tension.

Subsequently, as illustrated in FIG. 5(g), the surgeon pulls up the camera support tube 13 so as to be able to photograph an inside of the body cavity as widely as possible, and causes the camera unit 11 to be in contact with the end part of the cannula 31, which is in the intracorporeal side. Since the camera support tube 13 is tightly fastened by the valve 37 of the cannula 31 (refer to FIG. 4), the camera support tube 13 and the camera unit 11 maintain this state.

After installing the camera unit 11 in the body, as illustrated in FIG. 6, the camera-side cable 12 and the device-side cable 16 are joined by using the cable connector 15. Thereby, a local video of a treatment part is displayed on a display 118 by an endoscope control device 117, and a video of the entire of an inside of an organ 42, which is photographed by the camera unit 11, is displayed on the display 18 by the camera unit control device 17.

Figure 22:
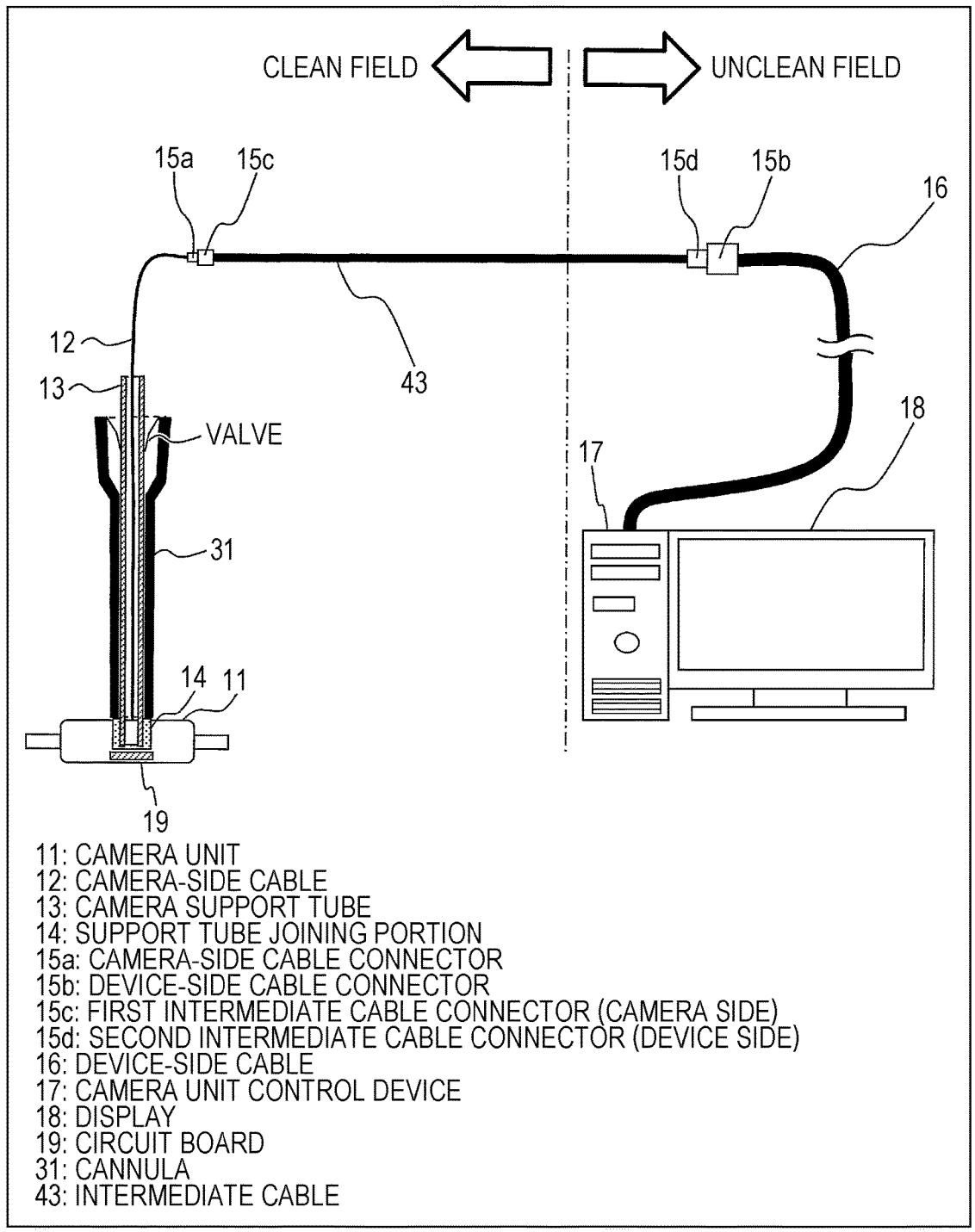
FIG. 22 is a view illustrating a modified example of Embodiment 1, which is a schematic view illustrating a state where an intermediate cable is added between a camera-side cable and a device-side cable.

Note that, as illustrated in FIG. 22, it is desirable that, for connection of the camera-side cable 12 and the device-side cable 16, an intermediate cable 43 (third cable), which connects them, is provided therebetween. This makes it possible to convert cable diameters of the camera-side cable 12 which is extra-fine and the device-side cable 16 which is thick and thickness of the cable connectors stepwisely, so that it is possible to make a configuration with required minimum use of a cable having a fine diameter, which has relatively slow transmission speed, resulting that transmission speed is able to be increased and a high-resolution image is able to be obtained. Moreover, as illustrated in FIG. 22, by fitting the camera-side cable connector 15a and a first intermediate cable connector 15c, the camera-side cable 12 and the intermediate cable 43 are connected. Further, by fitting the device-side cable connector 15b and a second intermediate cable connector 15d, the device-side cable connector 16 and the intermediate cable 43 are connected. In the case of converting the cable diameters or the thickness of the cable connectors stepwisely in this example, it is desirable to set that the outer diameter of the camera-side cable 12<an outer diameter of the intermediate cable 43<the outer diameter of the device-side cable 16" and an outer diameter of the camera-side cable connector 15a≤an outer diameter of the first intermediate cable connector 15c<an outer diameter of the second cable connector 15d≤an outer diameter of the device-side cable connector 15b".

In addition, by using the intermediate cable 43, an exceptional effect that a clean field and an unclean field at a time of surgery is able to be separated effectively as illustrated in FIG. 22 is realized. That is, the camera-side cable 12, which is inserted into the body, is set to have a required minimum length from a viewpoint of the transmission speed, which is described above, and in order to facilitate handling at a time of installation, and the intermediate cable 43, which has been subjected to sterilization treatment in advance, is used therefrom as far as entering in the unclean field after exceeding the clean field. This makes it possible to perform fitting of the camera-side cable connector 15a and the first intermediate cable connector 15c in the clean field, so that cleanliness is able to be maintained. On the other hand, the second intermediate cable connector 15d is fit to the device-side cable connector 15b which is in the unclean field, becomes unclean, and is treated as an unclean tool after the fitting. Accordingly, it is possible to be completely separated from clean tools.

Note that, a part included in the "clean field" in the in-body monitoring camera system is kept to have cleanliness by being subjected to sterilization treatment. On the other hand, a part included in the "unclean field" is not subjected to the sterilization treatment or enters in the unclean field after the sterilization treatment is applied.

Note that, it is desirable that connection strength (fitting strength) when connecting (fitting) the camera-side cable 12 and the intermediate cable 43 or the device-side cable 16 with the cable connector 15 is set to be smaller than the adhesive strength of the adhesively fixing part for adhesively fixing the camera-side cable 12 and the camera unit 11.

This is because, when large force which is not anticipated at a time of normal use is applied to the cable, the connecting (fitting) part with the cable connector 15 comes off first, and thereby a possibility that a body wall of a patient is damaged by breakage of the adhesively fixing part or the camera unit 11 drawn in a direction toward outside the body is eliminated, and thus safety is enhanced. In addition, it is possible to prevent an accident that, for example, a surgeon or an assistant stumbles over the cable and falls or the camera unit control device 17 is drawn and falls from a stand.

Specifically, it is desirable that the strength of connecting (fitting) the cables to each other with the cable connector 15 is set to be, for example, 30 N (newton) or less, which is smaller than the adhesive strength of the adhesively fixing part. Furthermore, as an optimal range, it is desirable to perform setting within a range from 4 N to 10 N. By setting within this range, it is possible to perform connection without applying excessively large force at a time of the connection, and it is not necessary to apply excessively large force also at a time of disconnection.

Moreover, by setting fitting strength of the device-side cable connector 15b and the second intermediate cable connector 15d, which are in the unclean field, and fitting strength of the device-side cable 16 and the camera unit control device 17 with a cable connector (not illustrated) which is on a side of the camera unit control device 17 of the device-side cable 16 to be larger than fitting strength of the camera-side cable connector 15a and the first intermediate cable connector 15c (for example, 50 N to 100 N), it is possible to set so that, when an unanticipated force is applied to the cable, the connection of the camera-side cable 12 and the intermediate cable 43 (fitting of the camera-side cable connector 15a and the first intermediate cable connector 15c), which is in the clean field, is always disconnected first. On the contrary, for example, if the connection of the intermediate cable 43 and the device-side cable 16 (fitting of the device-side cable connector 15b and the second intermediate cable connector 15d), which is in the unclean field, is disconnected first, a risk occurs that a part of the intermediate cable 43, which is in the unclean field, and the second intermediate cable connector 15d enter in the clean field in reaction. Therefore, for securing safety at a time of surgery, it is exceptionally effective that the connection in the clean field is disconnected first. Note that, in a case where the connection in the clean field is disconnected, and then the part of the intermediate cable 43, which is in the clean field, in other words, a part of the intermediate cable 43, which has a predetermined length from the fitting part of the camera-side cable connector 15a and the first intermediate cable connector 15c (clean part) and the first intermediate cable connector 15c are in contact with the unclean field, what is required is only replacing the intermediate cable 43 (including the first intermediate cable connector 15c) with a clean one, so that it is safe. Moreover, in a case where, when the cable connector is composed of an independent single part, the cable connector becomes in contact with the unclean field together with the clean side of the intermediate cable 43, what is required is only replacing the intermediate cable 43 and the cable connector with clean ones.

In addition, it is desirable that the camera-side cable 12 is set to be substantially short compared to a length of the sum of the camera-side cable 12 and the aforementioned clean part (about 1 m). Specifically, it is desirable that the camera-side cable 12 has a length of a half of or less than the sum of the camera-side cable 12 and the aforementioned clean part, that is, a length of 50 cm at longest. This makes it possible to prevent the camera-side cable 12 from entering in the unclean field.

Furthermore, though description has been given in the above-described example for a case where the camera-side cable 12 and the device-side cable 16 are connected with the intermediate cable 43, it is desirable that the camera-side cable 12 is set to be substantially short compared to the length of the sum of the camera-side cable 12 and the clean part (about 1 m) also in a case where the camera-side cable 12 and the device-side cable 16 are directly connected. In this case, the clean part is a part of the device-side cable 16, which has a predetermined length from a fitting part of the camera-side cable connector 15a and the device-side cable connector 15b.

As above, while applying treatment with the forceps 33a and the forceps 33c with a working region (local region) observed in an enlarged manner on the display 118, the surgeon is able to grasp states outside the working region (motion of forceps outside the working region, a bleeding place, a residue such as gauze, and the like) on the display 18.

Then, the camera unit 11 and the camera support tube 13 are joined with high mechanical strength, so that supporting force of the camera unit 11 is higher than conventional one. Further, since the camera-side cable 12 is led out to the outside of the body through the inner part of the camera support tube 13, after the camera unit 11 and the camera support tube 13 are joined, there is no possibility that a burden is applied to the camera-side cable 12, nor that the camera-side cable 12 is exposed inside the body or in contact with the body wall 41. This makes it possible to enhance certainty of electrical connection of the camera-side cable 12 and the circuit board 19 (a waterproof property and an antifouling property of the connection part). As above, it is possible to realize a reliable in-body monitoring camera system.

Furthermore, the surgeon is able to operate the camera support tube 13 according to a situation to thereby change an orientation (visual field direction) of the camera unit 11. Specifically, by utilizing elastic force of the body wall 41, it is possible to incline the camera support tube 13 to thereby change the orientation of the camera unit 11. At this time, since, when the surgeon release his/her hand from the camera support tube 13, the orientation returns to the original one with the elastic force of the body wall 41, it is possible to enhance working efficiency of the surgeon. Moreover, both of the cannula 31 and the camera support tube 13 inserted thereinto are cylindrical tubes, so that it is possible to easily rotate the camera support tube 13 in a circumferential direction. This makes it possible for the surgeon to change the orientation of the camera unit 11 without applying a burden to the body wall 41. In addition, the camera support tube 13 is held so as to be movable in a longitudinal thereof (extending direction of the tube) by the cannula 31, so that it becomes possible for the surgeon also to change zooming for imaging, without applying a burden to the body wall 41, by thrusting the camera support tube 13 toward inside the body or pulling it up toward outside the body. As above, it is possible to realize an in-body monitoring camera system which is easy to use.

Though the cannula 31 and the camera support tube 13 are fixed by the valve inside the cannula 31 in Embodiment 1, in a case where a common cannula having no valve is used, the cannula and the camera support tube 13 may be fixed with a tape.

(Separation of the Camera Unit 11 and the Camera Support Tube 13)

Next, a method of separating the camera unit 11 and the camera support tube 13 will be described. First, the surgeon draws the camera support tube 13 in a direction toward outside the body in a state where the gripping portions 22 of the camera unit 11 in the body are gripped by the forceps 33a and the forceps 33c, and pulls out the camera support tube 13 from the support tube joining portion 14 of the camera unit 11. Next, the surgeon pulls out the camera support tube 13 from the cannula 31 to separate the camera support tube 13 and the camera-side cable 12, and thereafter leads out the camera unit 11 and the camera-side cable 12 to the outside of the body through the trocar 32a and the trocar 32b.

Note that, similarly also in the case of separating the camera unit 11 and the camera support tube 13, it is desirable that fitting strength of the camera support tube 13 and the support tube joining portion 14 is smaller than the adhesive strength of the adhesively fixing part of the camera-side cable 12 and the camera unit 11. If the fitting strength of the camera support tube 13 and the support tube joining portion 14 is larger than the adhesive strength of the adhesively fixing part, it is necessary to apply large force when disconnecting the camera support tube 13 from the support tube joining portion 14, so that a risk that the adhesively fixing part is broken occurs. When the fitting strength is set to be in a range of, for example, 3 N to 6 N, the disconnection is able to be performed without applying excessive force, and an impact of disconnection of the camera support tube 13 is transmitted to a hand, so that an exceptional effect that separation is able to be performed safely without applying excessive force continuously is realized.

Note that, though the camera-side cable connector 15a passes through the inside of the body at a time of collection, cleanliness is kept as illustrated in FIG. 22, so that there is no problem.

Embodiment 2

Though the cannula and the camera support tube are formed separately in Embodiment 1, the camera support tube may have a function of the cannula or a function of the trocar. Description will be given below for the case of the cannula, but, needless to say, the similar is also applied to the case of the trocar. FIG. 7(a) is a perspective view of a camera support tube of Embodiment 2, and FIG. 7(b) is a sectional view thereof. As illustrated in FIGS. 7(a) and (b), a camera support tube 35 is funnel-shaped similarly to the cannula, one end part (extracorporeal side) is thicker than the other end part (intracorporeal side), and the locking holes 123 (recesses) are provided in the other end part (intracorporeal side). Moreover, the locking holes 123 may be provided in a part (at least two sites) of an outer periphery of the camera support tube 35 as illustrated in FIG. 7(a) and FIG. 7(c), or the groove-shaped recess 723 which is formed around an outside surface thereof may be provided in the end part of the camera support tube 35 and a ridge-like protrusion which is formed around along an inside surface of the opposing support tube joining portion 14 may be provided, as illustrated in FIG. 7(e). This is more desirable since it is not necessary to perform an operation of matching positions of the locking holes 123 and the locking pawls 23 when inserting the camera support tube 35, and it becomes easier to join the both, which is more desirable.

Moreover, in the case of forming a tip end part of the camera support tube 35 in a tapered shape in order to facilitate the insertion thereof, the tapered shape is able to be obtained by reducing thickness of the camera support tube 35, as illustrated in FIG. 7(f). At this time, by setting an inner diameter of the camera support tube 35 to be fixed and changing only an outer diameter (setting an external form to be smaller as being close to the tip end), when a tool is inserted into the camera support tube, it is not likely to happen, for example, that the tool is hooked midway (at a narrowed site) and becomes unable to be pulled out, so that it is more desirable.

FIG. 7(c) is a perspective view when the camera support tube of Embodiment 2 is combined with an obturator, and FIG. 7(d) is a sectional view thereof. As illustrated in FIGS.

7(c) and (d), in the case of inserting the camera support tube 35 into a body, an obturator 36 is inserted into the camera support tube 35, and a tip end (sharp part) of the obturator 36, which is exposed from the thinner end part (intracorporeal side) of the camera support tube 35, punctures a port (hole incised in the abdominal wall). Thereby, the camera support tube 35 is inserted into the body wall 41, and the camera support tube 35 is fixed in a contact manner by the body wall. In addition, the thicker end part of the camera support tube 35 is out of the body, so that there is no possibility that the camera support tube 35 falls out into the body, neither.

Furthermore, FIGS. 7(g) and (h) are perspective views in the case of combining the camera support tube of FIGS. 7(e) and (f) with the obturator, respectively. In this case as well, an effect similar to that of the case described in FIGS. 7(c) to (f) is realized.

(Method of Using and Effect of in-Body Monitoring Camera System in Embodiment 2)

Figure 9:
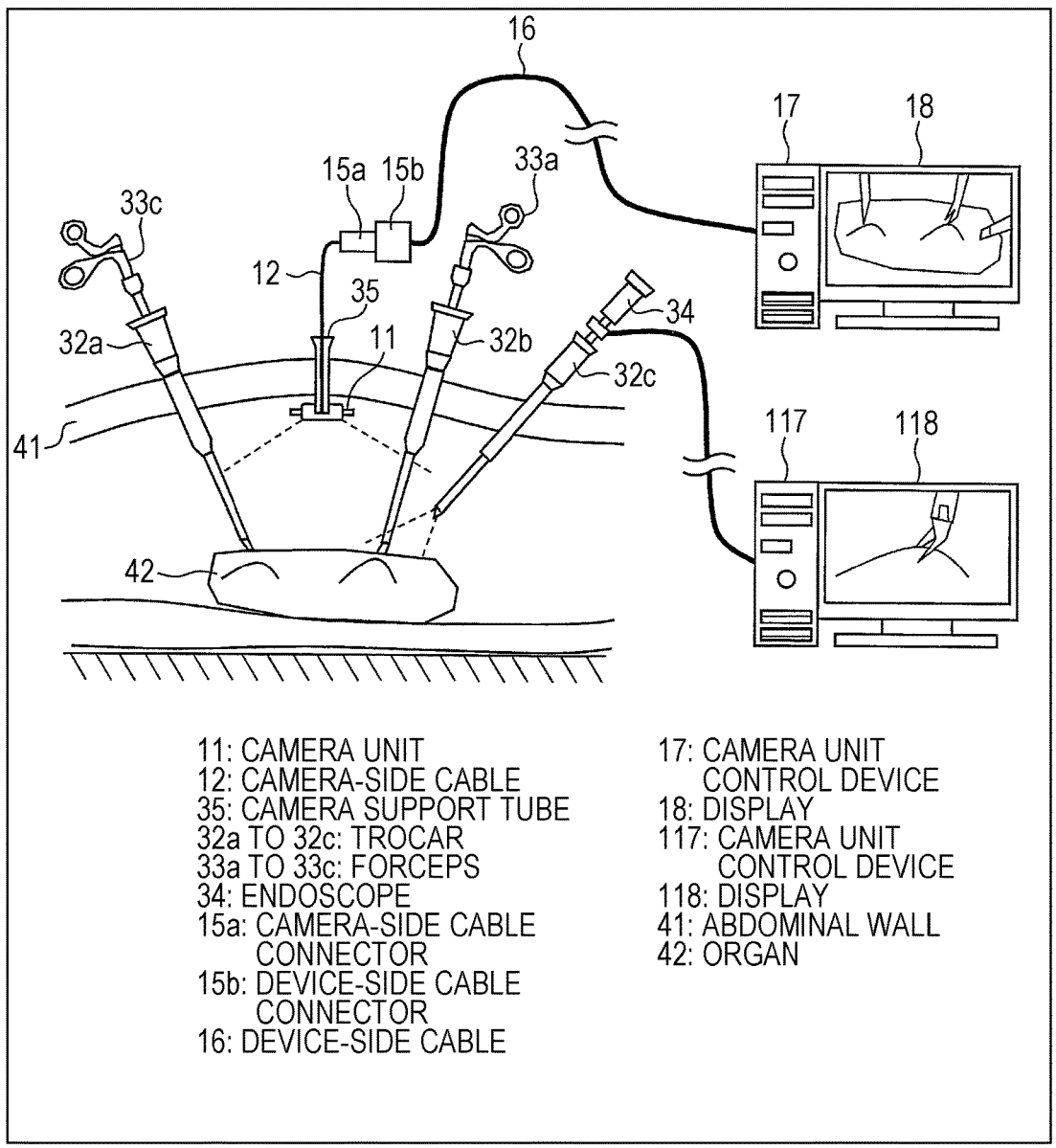
FIG. 9 is a schematic view illustrating a method of using the camera unit in Embodiment 2.
Figure 10:
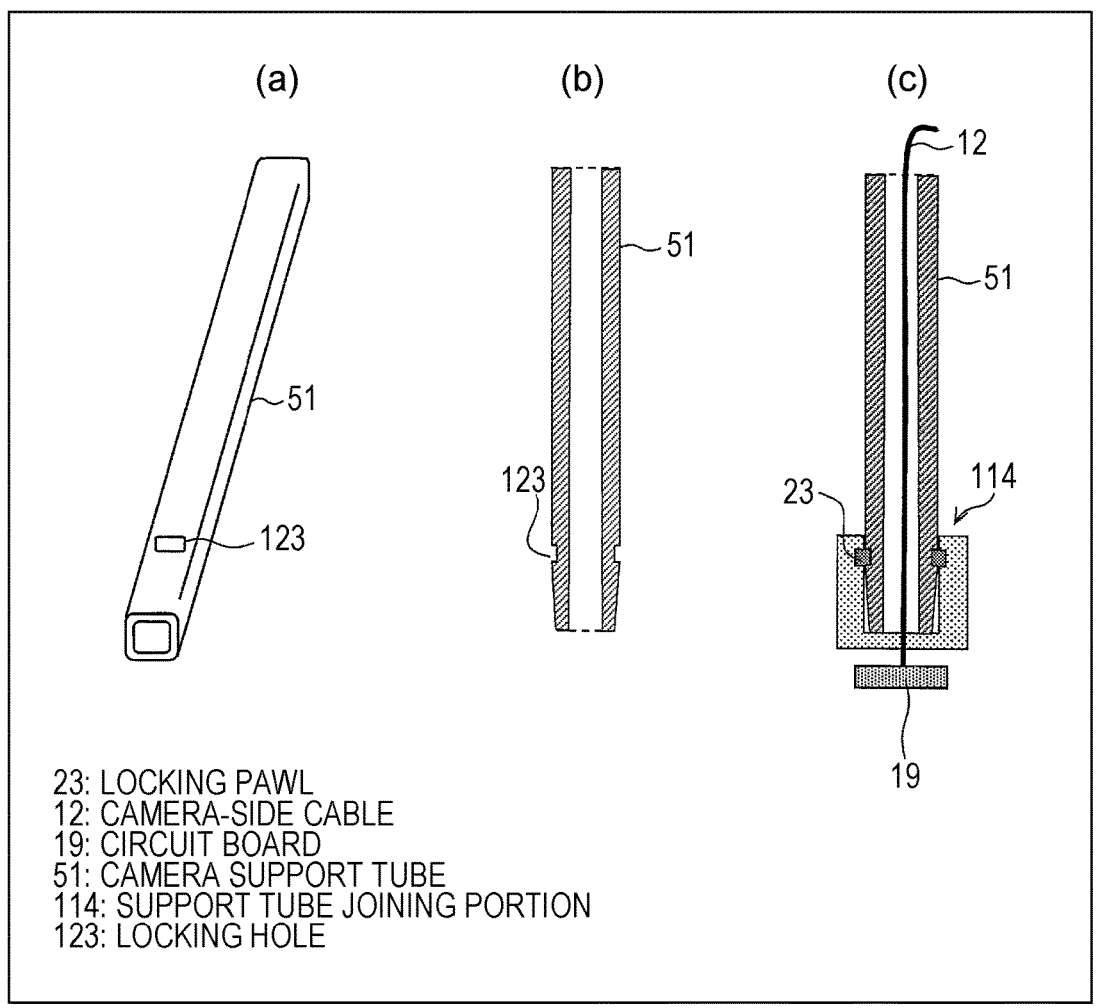
FIG. 10(a) is a perspective view of a camera support tube of Embodiment 3, (b) is a sectional view of (a), and (c) is a sectional view of a support tube joining portion of Embodiment 3.
Figure 11:
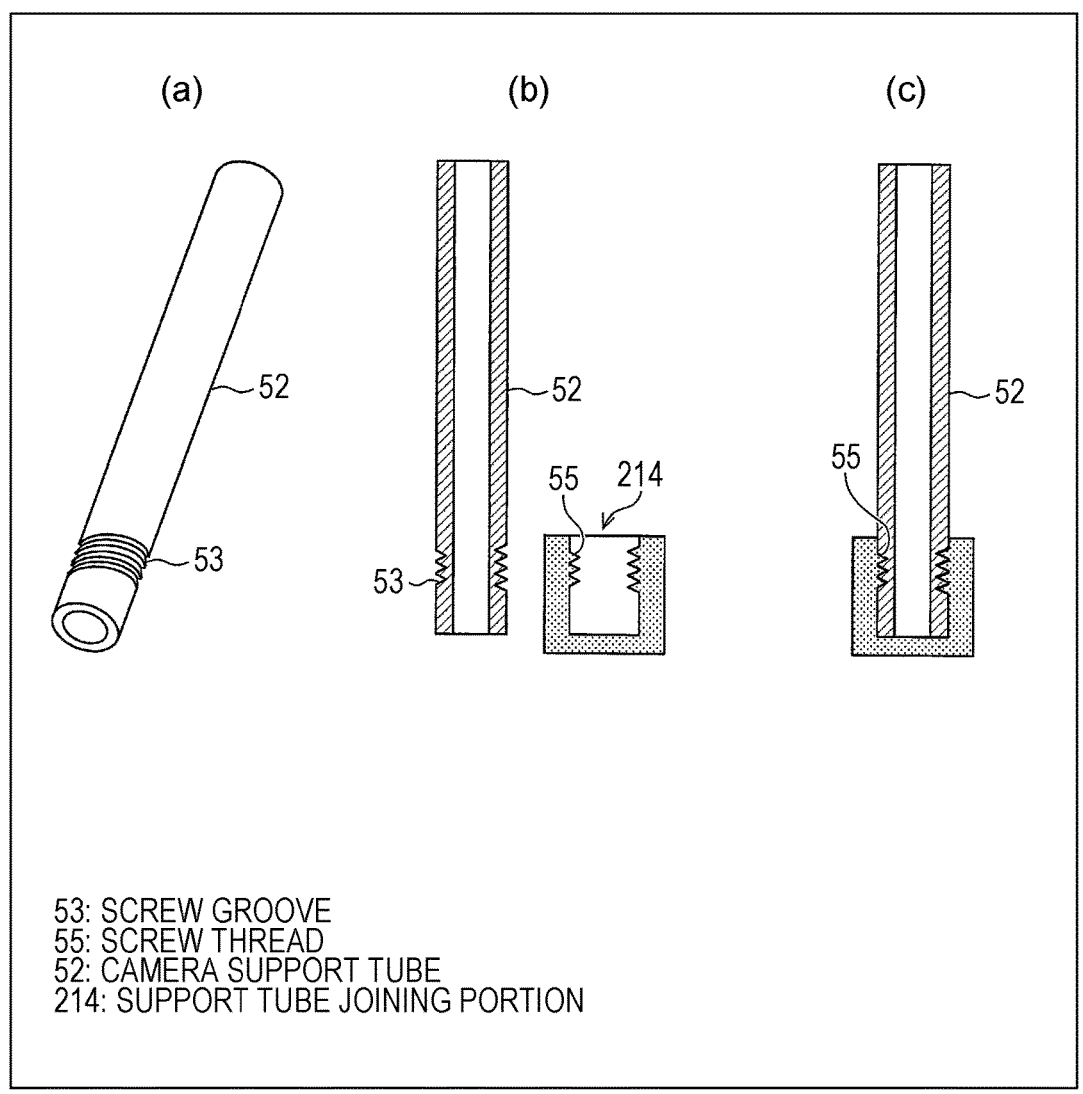
FIG. 11(a) is a perspective view of a camera support tube of Embodiment 4, (b) is a sectional view of the camera support tube and a support tube joining portion of Embodiment 4, and (c) is a sectional view illustrating a state where the camera support tube and the support tube joining portion of (b) are joined.
Figure 12:
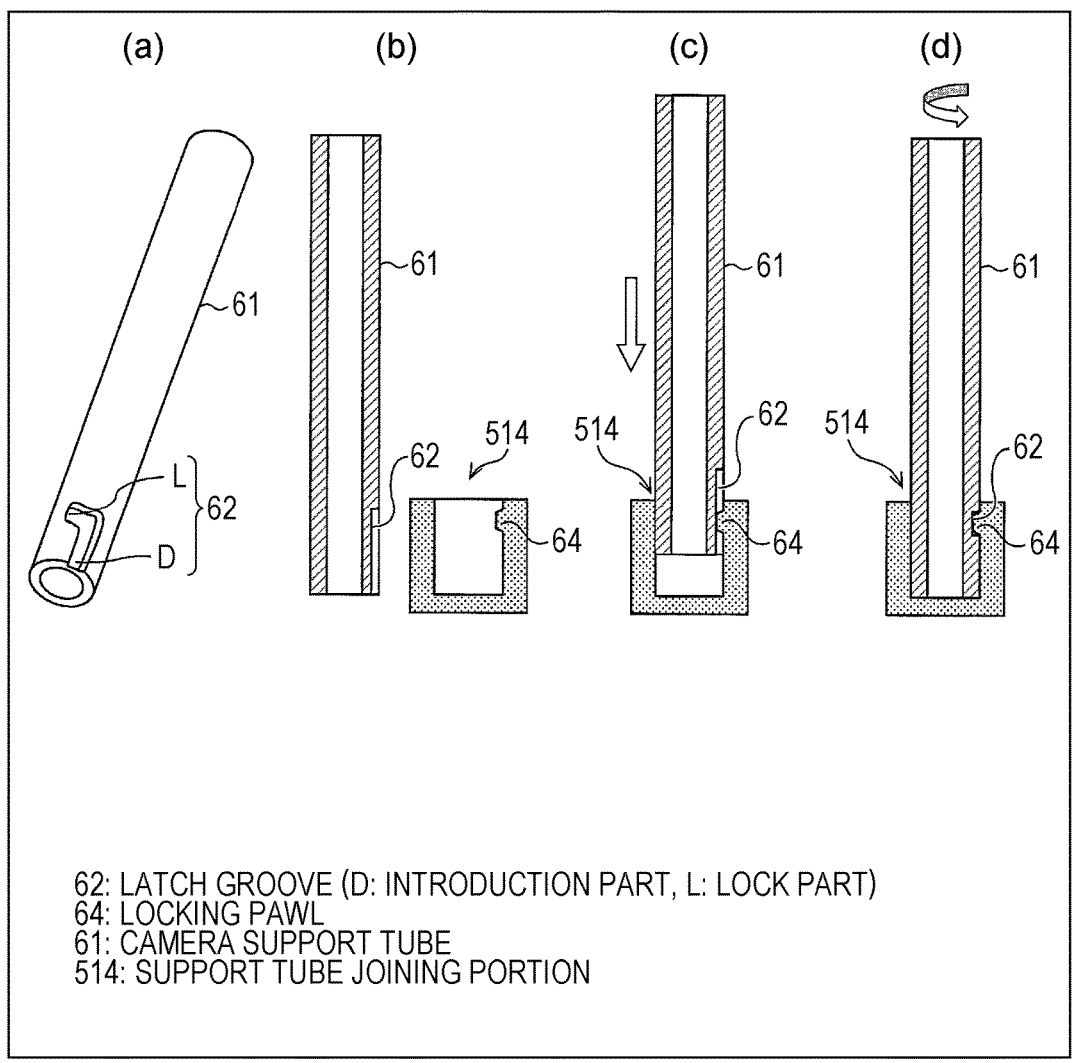
FIG. 12(a) is a perspective view of a camera support tube of Embodiment 5, (b) is a sectional view of the camera support tube and a support tube joining portion of Embodiment 5, and (c) and (d) are sectional views illustrating a method of joining the camera support tube and the support tube joining portion of (b).
Figure 13:
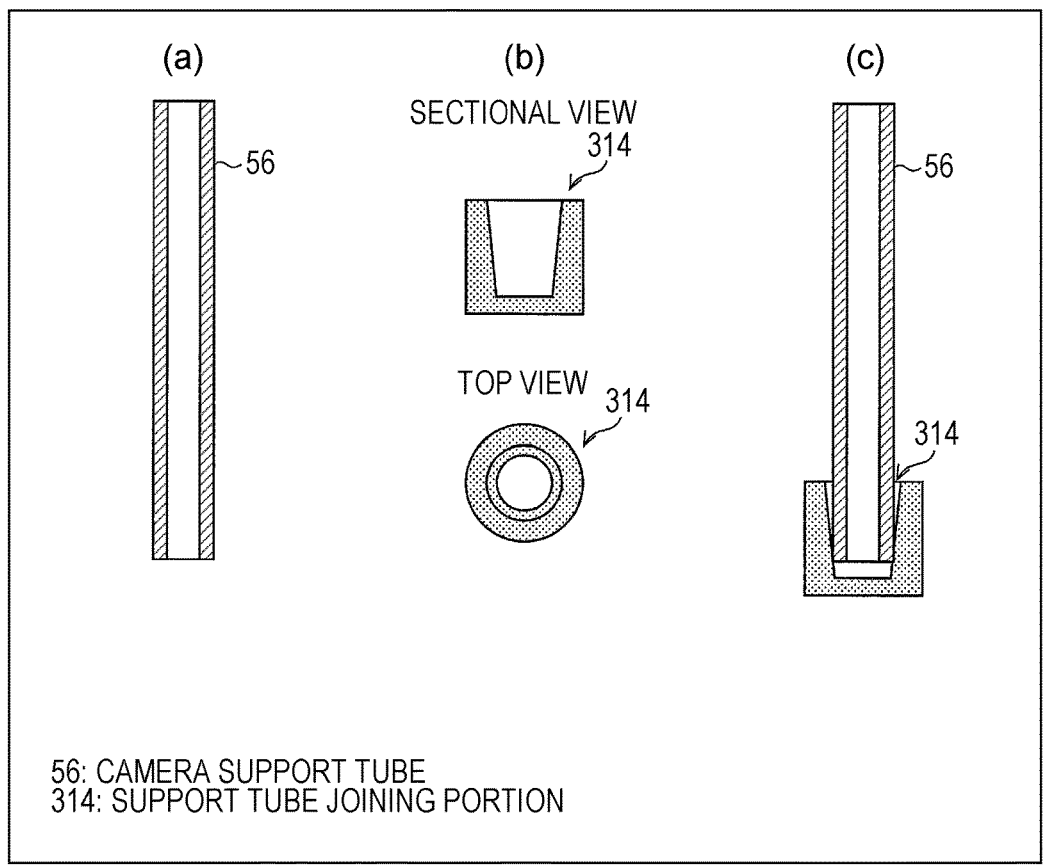
FIG. 13(a) is a sectional view of a camera support tube of Embodiment 6, (b) is a sectional view and a top view of a support tube joining portion of Embodiment 6, and (c) is a sectional view illustrating a state where the camera support tube of (a) and the support tube joining portion of (b) are joined.
Figure 14:
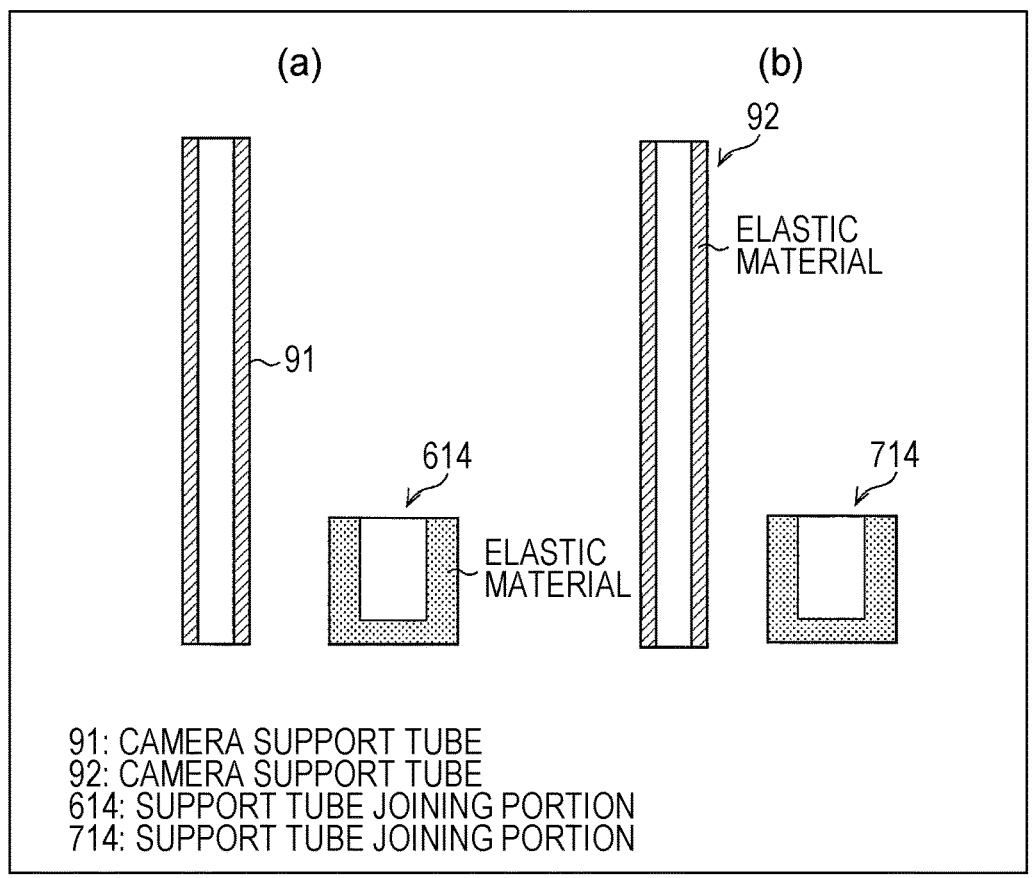
FIG. 14 is a sectional view illustrating a modified example of Embodiment 6.

FIGS. 8(a) to (g) are schematic views illustrating a method of installing the camera unit in a body in Embodiment 2, and FIG. 9 is a schematic view illustrating a situation of using an in-body monitoring camera system in Embodiment 2. Note that, the camera unit used in Embodiment 2 has the configuration illustrated in FIG. 2.

As illustrated in FIG. 8(a), first, a surgeon incises a body wall 41 for holes (ports) through which forceps or an endoscope is inserted into a body cavity, and inserts the trocars 32a to 32c into the ports. Further, a port is incised at a position in the body wall 41, from which an entire of an organ including an affected part is able to be seen, and the camera support tube 35 is inserted. Specifically, when a needle-shaped obturator punctures the port in a state where the obturator is inserted into the camera support tube 35, the camera support tube 35 is inserted into the body wall 41, and the camera support tube 35 is fixed in a contact manner by the body wall. Note that, from a viewpoint of low invasiveness, it is preferable that the camera support tube 35 has a caliber as small as possible. After at least one of the trocars 32a to 32c and the camera support tube 35 is inserted, the surgeon sends gas into the body through the trocar to distend the body cavity in advance for securing a space into which a tool is inserted.

Next, as illustrated in FIG. 8(b), the surgeon inserts the endoscope 34 into the body cavity through the trocar 32c, and inserts the camera unit 11 gripped with forceps 33a into the body cavity through the trocar 32b while observing inside the body by using the endoscope 34.

Then, as illustrated in FIG. 8(c), the surgeon operates the forceps 33a to move the camera unit 11 to a vicinity of the camera support tube 35 and inserts, for example, forceps 33b into the body cavity through the camera support tube 35. That is, the camera support tube 35 has an inner diameter which allows a tool used for pulling up a cable, such as the forceps 33b, to pass therethrough.

Next, as illustrated in FIG. 8(d), the surgeon pulls out the forceps 33b from the camera support tube 35 in a state where the camera-side cable 12 is held by the forceps 33b, and thereby leads out the camera-side cable 12 to the outside of the body. At this time, the camera unit 11 (the gripping portion 22 thereof) is in a state of being gripped by the forceps 33a.

Subsequently, as illustrated in FIG. 8(e), the surgeon inserts the forceps 33c into the body cavity through the trocar 32a, and then grips the gripping portions 22 in the both side surfaces of the camera unit 11 by the two forceps 33a and 33c so that the support tube joining portion 14 of the camera unit 11 and an opening of the camera support tube 35 are in parallel and proximate to each other.

Next, as illustrated in FIG. 8(f), by using the camera-side cable 12 as a guide, the surgeon inserts the end part of the camera support tube 35 into the support tube joining portion 14 of the camera unit 11 and joins the camera support tube 35 and the camera unit 11.

Subsequently, as illustrated in FIG. 8(g), the surgeon pulls up the camera support tube 35 so as to be able to photograph the inside of the body cavity as widely as possible.

After installing the camera unit 11 in the body, as illustrated in FIG. 9, the camera-side cable 12 and the device-side cable 16 are joined by using the cable connector 15. Thereby, a local video of a treatment part is displayed on the display 118 by the endoscope control device 117, and a video of the entire of the inside of the organ 42, which is photographed by the camera unit 11, is displayed on the display 18 by the camera unit control device 17.

Thereby, while applying treatment with the forceps 33a and the forceps 33c with a working region (local region) observed in an enlarged manner on the display 118, the surgeon is able to grasp states outside the working region (motion of forceps outside the working region, a bleeding place, a residue such as gauze, and the like) on the display 18.

Then, the camera unit 11 and the camera support tube are joined with high mechanical strength, so that supporting force of the camera unit 11 is higher than conventional one. Further, since the camera-side cable 12 is led out to outside of the body through an inner part of the camera support tube 35, after the camera unit 11 and the camera support tube 35 are joined, there is no possibility that a burden is applied to the camera-side cable 12, nor that the camera-side cable 12 is exposed inside the body or in contact with the body wall 41. This makes it possible to enhance certainty of electrical connection of the camera-side cable 12 and the circuit board 19 (a waterproof property and an antifouling property of the connection part). As above, it is possible to realize a reliable in-body monitoring camera system.

Furthermore, the surgeon is able to operate the camera support tube 35 according to a situation to thereby change the orientation (visual field direction) of the camera unit 11. Specifically, by utilizing elastic force of the body wall 41, it is possible to incline the camera support tube 35 to thereby change the orientation of the camera unit 11. At this time, since, when the surgeon release his/her hand from the camera support tube 35, the orientation returns to the original one with the elastic force of the body wall 41, it is possible to enhance working efficiency of the surgeon.

Furthermore, the camera support tube of Embodiment 2 does not need to have a tubular member passing through the inner part thereof like the cannula of Embodiment 1, and is able to make the caliber thereof small, and thus is excellent in low invasiveness. In addition, a step of inserting the camera support tube into the cannula in a state where the camera-side cable 12 is inserted into the camera support tube like in Embodiment 1 is not required in Embodiment 2, thus making it possible to enhance working efficiency of the surgeon.

Embodiment 3

The camera support tube is a cylindrical tube (a sectional surface thereof has a circular shape) in Embodiments 1 and 2, but there is no limitation thereto. FIG. 10(a) is a perspective view of a camera support tube of Embodiment 3, and FIG. 10(b) is a sectional view thereof. As illustrated in FIGS.

10(a) and (b), a camera support tube 51 may be also a tube having a quadrangular prism shape (a sectional surface thereof has a rectangular shape). One end part (intracorporeal side) of the camera support tube 51 is provided with the locking holes 123 (recesses). FIG. 10(c) is a sectional view of a support tube joining portion of the camera unit, which is used in Embodiment 3. As illustrated in FIG. 10(c), a support tube joining portion 114 of the camera unit has a hollow structure whose opening is square, and the locking pawls (protrusions) 23 are provided in an inner wall thereof. Then, by inserting the end part (intracorporeal side) of the camera support tube 51 into the support tube joining portion 114, the locking pawls 23 fit to the locking holes 123, and the camera unit and the camera support tube 51 are joined with high mechanical strength.

Since a sectional surface of the support tube joining portion 114 which is provided on the circuit board 19 has a square shape in Embodiment 3, it is possible to utilize a region around the support tube joining portion 114 with no waste, so that it is advantageous to miniaturization of the camera unit 11. In addition, there is also an effect that the camera support tube 51 which has the quadrangular prism shape is difficult to roll. Further, there is also an effect that, after connection with the camera unit, the camera unit does not perform rotation, which is not intended, at the connection part.

Embodiment 4

The locking holes of the camera support tube are fit to the locking pawls of the support tube joining portion in Embodiments 1 and 2, but there is no limitation thereto. FIG. 11(a) is a perspective view of a camera support tube of Embodiment 4, FIG. 11(b) is a sectional view of the camera support tube and a support tube joining portion of Embodiment 4, and FIG. 11(c) is a sectional view illustrating a state where the camera support tube and the support tube joining portion in Embodiment 4 are joined. As illustrated in FIGS. 11(a) and (b), a camera support tube 52 is a cylindrical tube, and a screw groove 53 is provided in one end part (intracorporeal side) thereof. A support tube joining portion 214 of the camera unit has a hollow structure whose opening is circular, and a screw thread 55 is provided in an inner wall thereof.

In order to facilitate insertion of the camera support tube into the support tube joining portion, it is desirable to make an outer diameter of a tip end part of the camera support tube 52 small. For example, as illustrated in FIGS. 19(a) to (c), a tapered shape is able to be obtained by reducing thickness of the camera support tube 52. At this time, by setting an inner diameter of the camera support tube 52 to be fixed and changing only the outer diameter (setting an external form to be smaller as being close to the tip end), when a tool is inserted into the camera support tube, it is not likely to happen, for example, that the tool is hooked midway (at a narrowed site) and becomes unable to be pulled out, so that it is more desirable.

Then, as illustrated in FIG. 11(c), by fitting the screw groove 53 of the camera support tube 52 to the screw thread 55 of the support tube joining portion 214, the camera unit and the camera support tube 52 are joined with high mechanical strength. Specifically, while gripping the camera unit by two pairs of forceps so that the support tube joining portion 214 and an opening of the camera support tube 52 are in parallel and proximate to each other, the surgeon rotates (screws in a first direction) an end part of the camera support tube 52 (extracorporeal side) and screws the camera support tube 52 into the support tube joining portion 214.

After finishing photographing, the surgeon counter-rotates (screws in a second direction opposite to the first direction) the camera support tube 52 in a state of gripping the gripping portions 22 of the camera unit 11 in the body with the forceps 33a and the forceps 33c, and disconnects the camera support tube 52 from the support tube joining portion 214 of the camera unit 11.

In Embodiment 4, it is possible to further increase joining strength of the camera unit and the camera support tube, and separation of the camera unit and the camera support tube is also facilitated.

Embodiment 5

The camera support tube is provided with the locking holes in Embodiments 1 and 2, and the locking holes may have a groove shape. FIG. 12(a) is a perspective view of a camera support tube of Embodiment 5, FIG. 12(b) is a sectional view of the camera support tube and a support tube joining portion of Embodiment 5, and FIGS. 12(c) and (d) are sectional views illustrating a method of joining the camera support tube and the support tube joining portion in Embodiment 5. As illustrated in FIGS. 12(a) and (b), a camera support tube 61 is a cylindrical tube, and a latch groove 62 which extends from a vicinity of one opening part in an L-shaped manner when viewed in a longitudinal direction is provided in a surface thereof. The latch groove 62 is composed of an introduction part D which extends in the longitudinal direction and a lock part L which bends by 90 degrees with respect to the introduction part D. A support tube joining portion 514 of the camera unit has a hollow structure whose opening is circular, and a locking pawl 64 is provided at one site in an inner wall thereof. By thrusting the camera support tube 61 until the locking pawl 64 reaches the bent part of the latch groove 62 in a state where the locking pawl 64 is fit to the introduction part D of the latch groove 62 as illustrated in FIG. 12(c), and then rotating the camera support tube 61 to cause the locking pawl 64 to be hooked on the lock part L as illustrated in FIG. 12(d), the camera unit and the camera support tube 61 are joined with high mechanical strength.

Embodiment 6

In Embodiments 1 and 2, the camera support tube is provided with the locking holes (recesses) and the support tube joining portion is provided with the locking pawls (protrusions), but a configuration that such locking holes (recesses) nor locking pawls (protrusions) are not provided may be possible. FIG. 13(a) is a sectional view of a camera support tube of Embodiment 6, FIG. 13(b) is a sectional view and a top view of a support tube joining portion of Embodiment 6, and FIG. 13(c) is a sectional view illustrating a state where the camera support tube and the support tube joining portion in Embodiment 6 are joined. As illustrated in FIG. 13(a), a camera support tube 56 is a cylindrical tube, and neither recess nor protrusion is provided in a surface thereof. As illustrated in FIG. 13(b), a support tube joining portion 314 of the camera unit has a hollow structure whose opening is circular, and neither protrusion nor recess is provided in an inner wall thereof. However, the support tube joining portion 314 has the inner wall inclined, which has a tapered shape whose hole diameter is small as being apart from the opening. Then, as illustrated in FIG. 13(c), by thrusting the camera support tube 56 into the support tube joining portion 314, the camera unit and the camera support tube 56 are joined with frictional contact.

Moreover, as illustrated in FIG. 14(a), it is also possible to provide a configuration in which a support tube joining portion 614 has a hollow structure whose opening is circular and an inner wall thereof is formed of an elastic material such as rubber. In this case, by thrusting a camera support tube 91 (in which neither recess nor protrusion is provided in a surface thereof) into the support tube joining portion 614, the camera support tube 91 is fastened with an elastic property of the support tube joining portion 614, and the camera unit and the camera support tube 91 are joined with high mechanical strength.

In addition, as illustrated in FIG. 14(b), it is also possible to form a camera support tube 92 (in which neither recess nor protrusion is provided in a surface thereof) with an elastic material such as rubber. In this case, by thrusting the camera support tube 92 into a support tube joining portion 714, the camera support tube 92 is fastened with its own elastic property, and the camera unit and the camera support tube 92 are joined with high mechanical strength.

Figure 15:
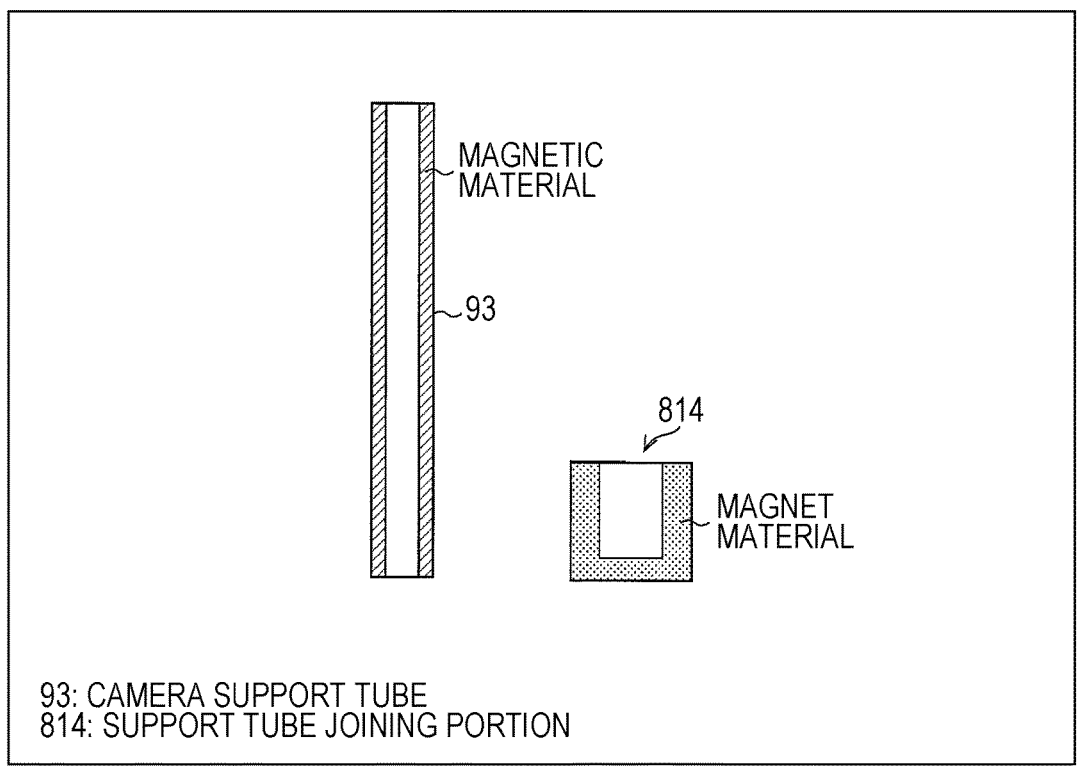
FIG. 15 is a sectional view of another modified example of Embodiment 6.
Figure 16:
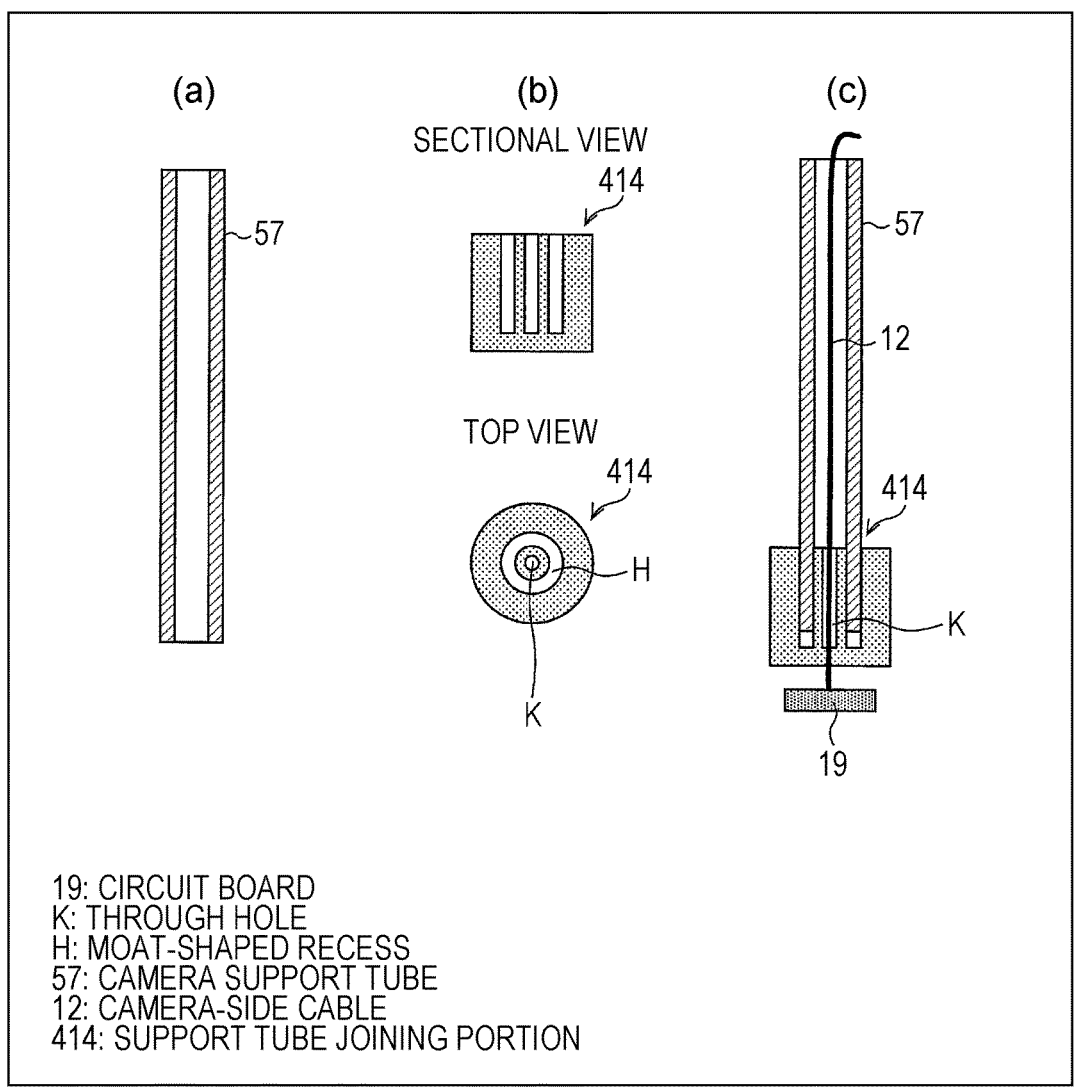
FIG. 16(a) is a sectional view of a camera support tube of Embodiment 7, (b) is a sectional view and a top view of a support tube joining portion of Embodiment 7, and (c) is a sectional view illustrating a state where the camera support tube of (a) and the support tube joining portion of (b) are joined.
Figure 17:
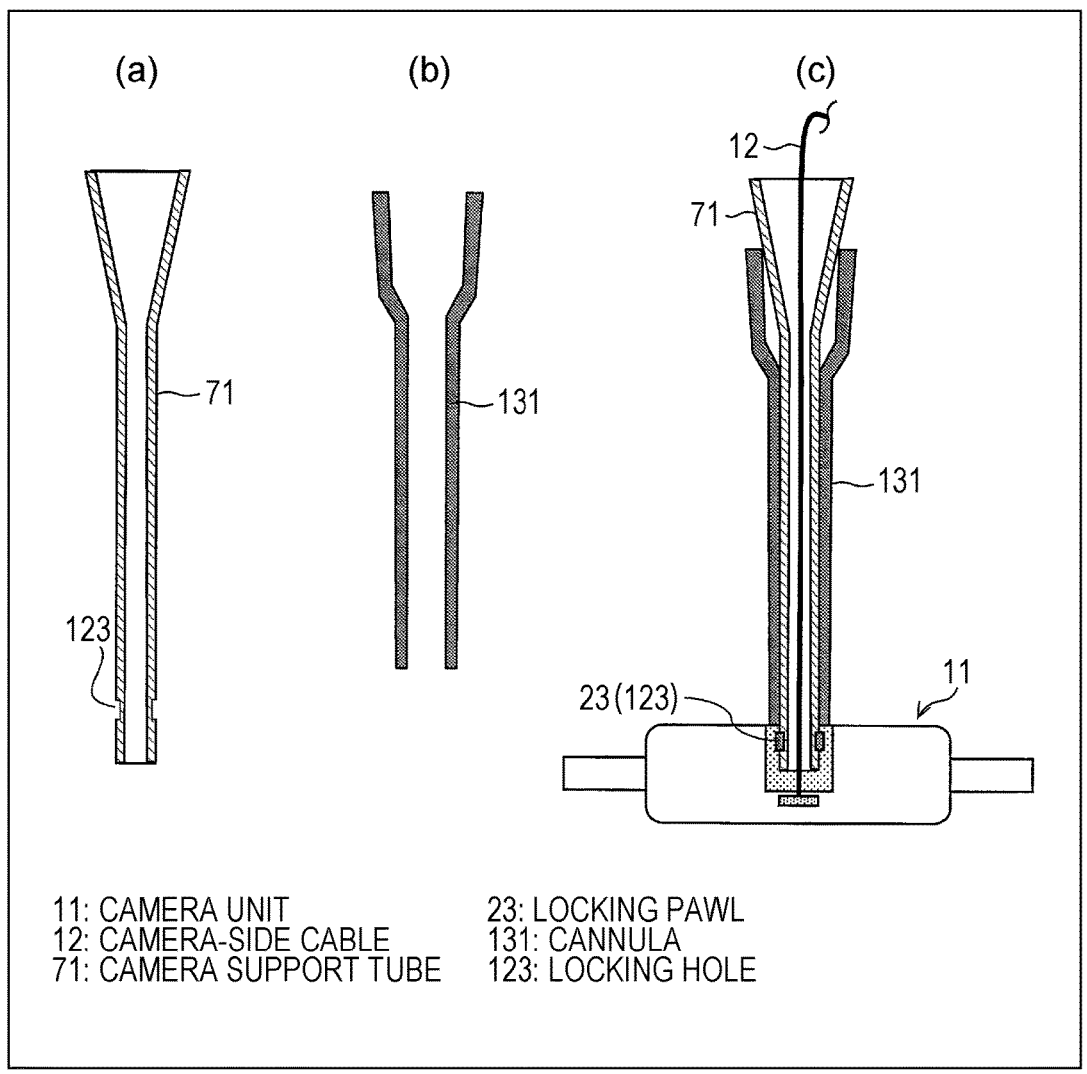
FIG. 17(a) is a sectional view of a camera support tube of Embodiment 8, (b) is a sectional view of a cannula of Embodiment 8, and (c) is a sectional view illustrating a state where the camera support tube of (a) is inserted into the cannula of (b).
Figure 18:
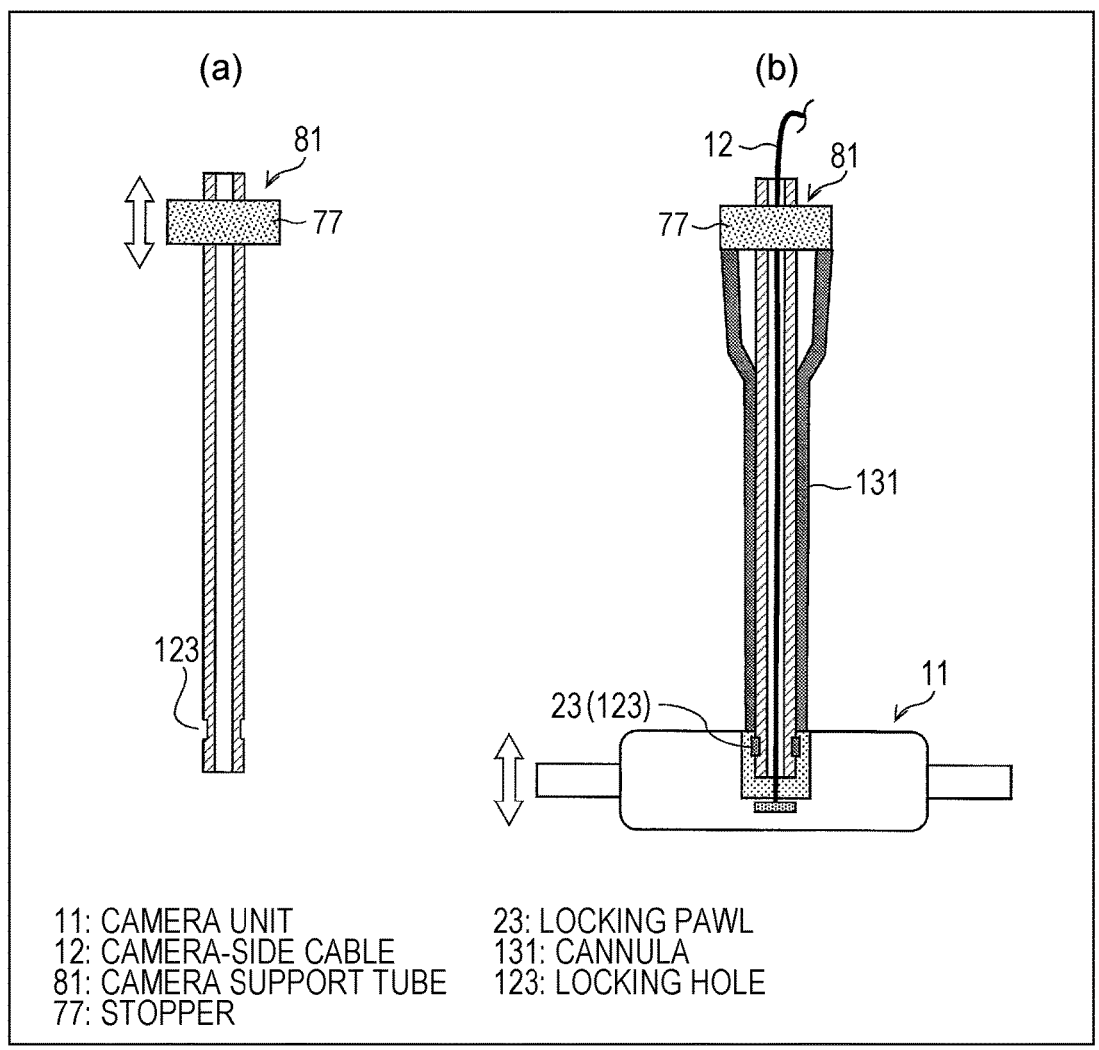
FIG. 18 is a sectional view illustrating a modified example of Embodiment 8.
Figure 19:
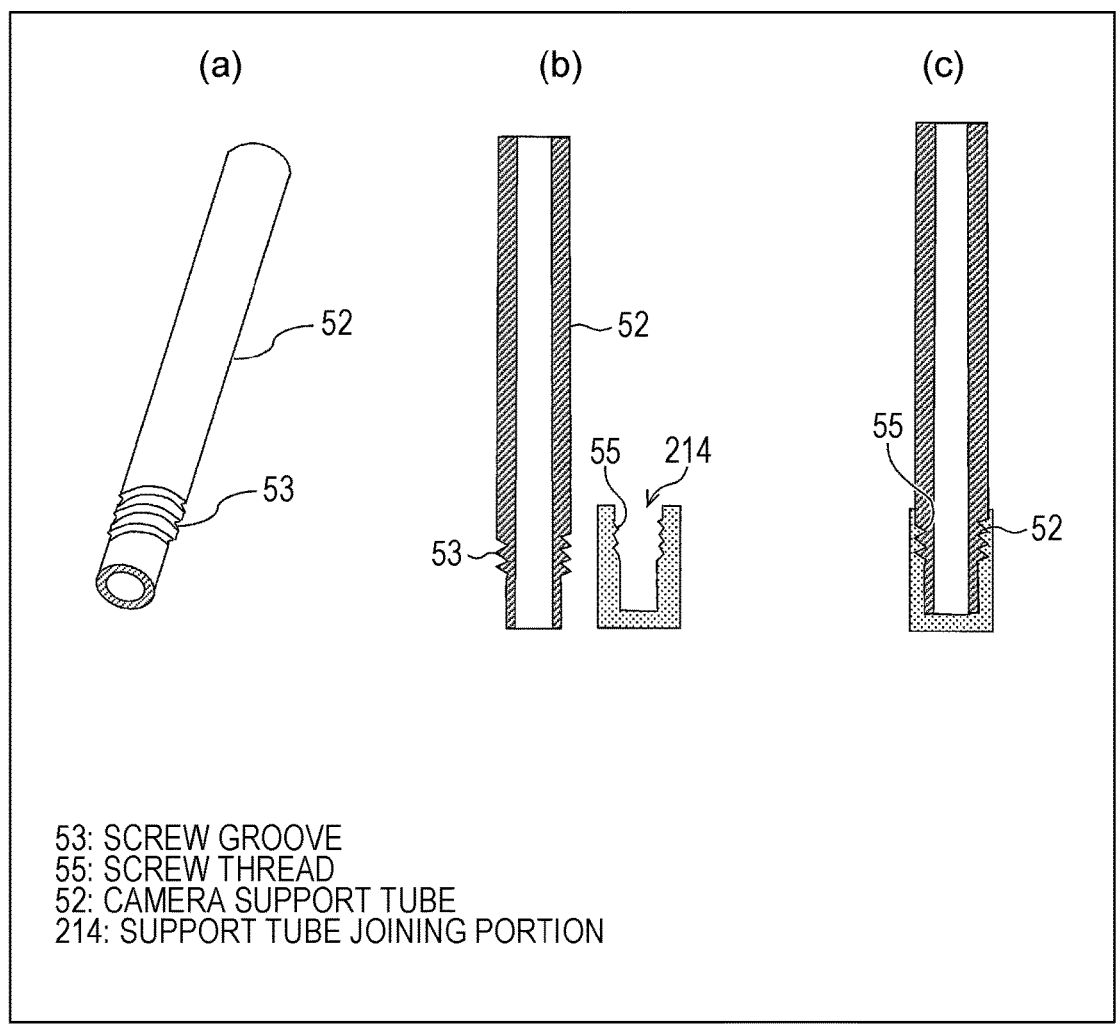
FIG. 19(a) is a perspective view of a camera support tube of a modified example of Embodiment 4, (b) is a sectional view of the camera support tube and a support tube joining portion of the modified example of Embodiment 4, and (c) is a sectional view illustrating a state where the camera support tube and the support tube joining portion of (b) are joined.
Figure 20:
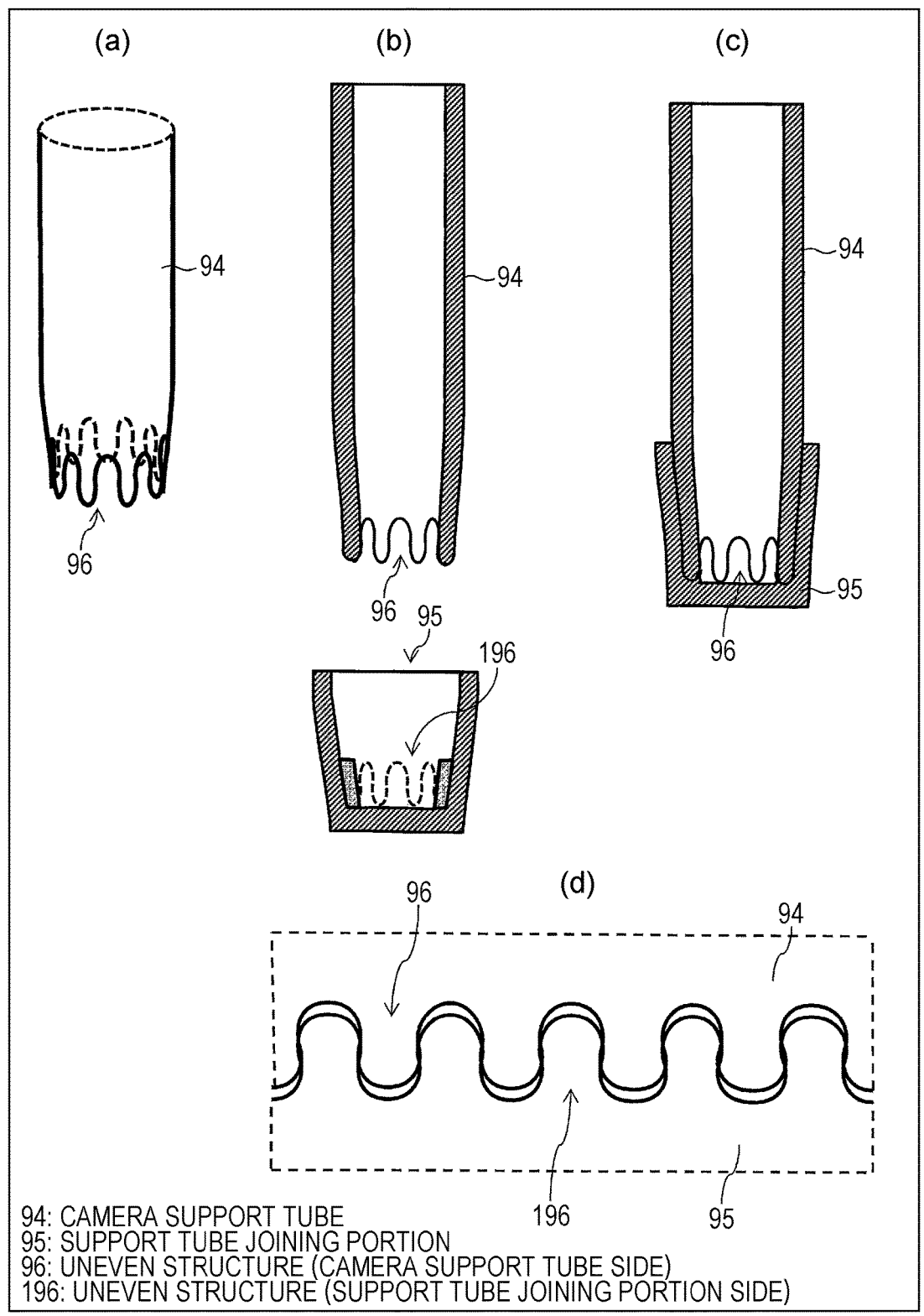
FIG. 20(a) is a perspective view of a main part of a camera support tube of Embodiment 9, (b) is a sectional view of a main part of the camera support tube and a support tube joining portion of Embodiment 9, (c) is a sectional view illustrating a state where the camera support tube and the support tube joining portion in Embodiment 9 are joined, and (d) is a development view of a corrugated part of the camera support tube and the support tube joining portion.
Figure 21:
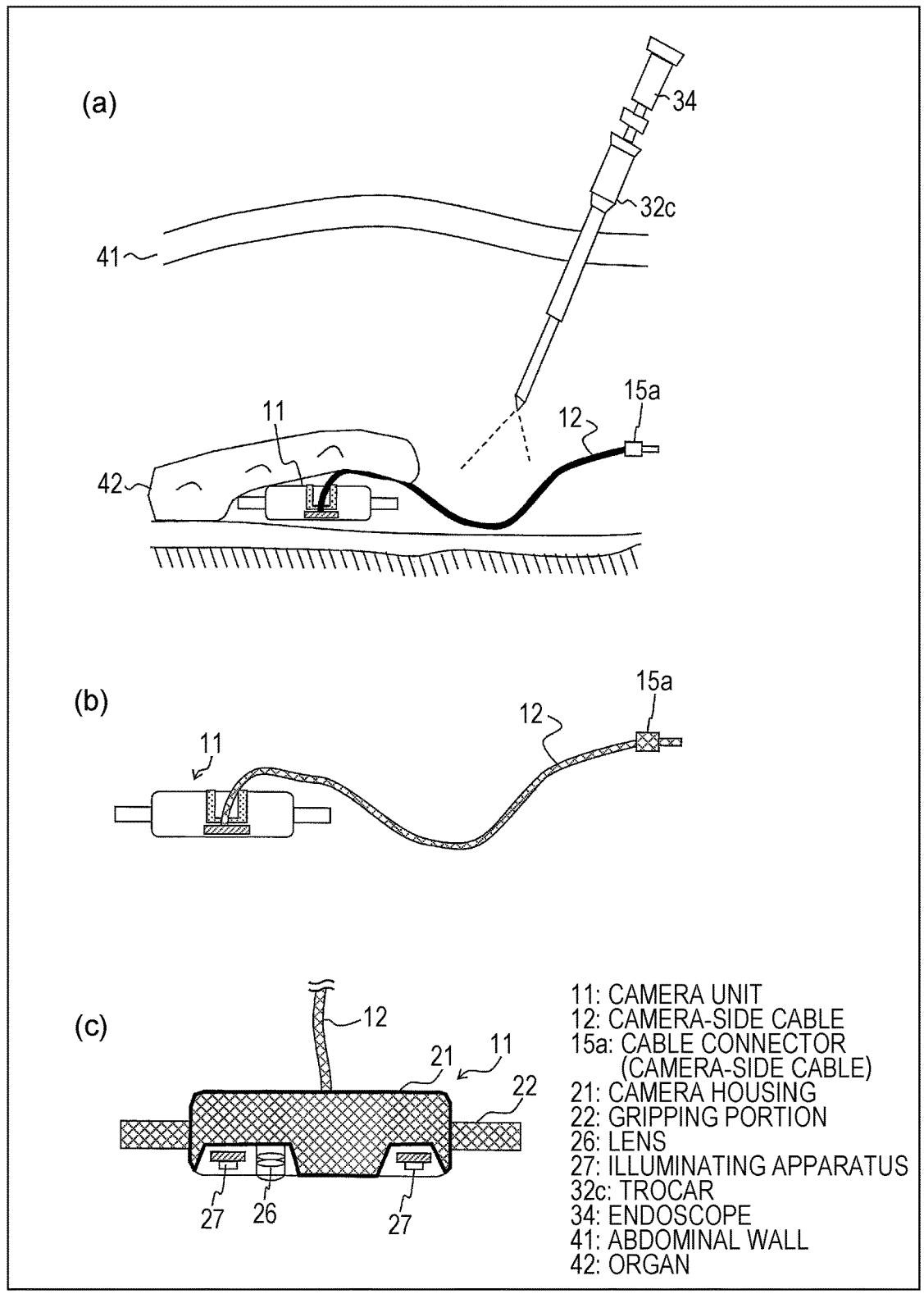
FIG. 21(a) is a schematic view illustrating a method of searching for a camera, which has fallen down, in Embodiment 1, and (b) is a view illustrating a colored part of a camera unit of Embodiment 10.

Furthermore, as illustrated in FIG. 15, it is also possible that a camera support tube 93 (in which neither recess nor protrusion is provided in a surface thereof) is formed of a magnetic material including a magnetic substance, such as iron or nickel, and an inner wall and a bottom part of a support tube joining portion 814 which has a hollow structure whose opening is circular are formed of a magnet material. In this case, when inserting the camera support tube 93 into the support tube joining portion 814, the camera unit and the camera support tube 93 are joined with high mechanical strength due to magnetic force between the camera support tube 93 and the support tube joining portion 814. Note that, it is desirable that the magnetic material used for the camera support tube 93 does not act as a magnet (permanent magnet) so that the camera support tube 93 does not attract a surgical tool such as forceps. Note that, it is also possible that the inner wall in an inlet side of the support tube joining portion 814 is formed of a non-magnetic body and the inner wall in a deeper side and the bottom part are formed of a magnet material so that the support tube joining portion 814 does not attract a surgical tool such as forceps.

Embodiment 7

In Embodiments 1 and 2, the support tube joining portion has the hollow structure whose opening is circular, but there is no limitation thereto. FIG. 16(a) is a sectional view of a camera support tube of Embodiment 7, FIG. 16(b) is a sectional view and a top view of a support tube joining portion of Embodiment 7, and FIG. 16(c) is a sectional view illustrating a state where the camera support tube and the support tube joining portion of Embodiment 7 are joined. As illustrated in FIG. 16(a), a camera support tube 57 is a cylindrical tube, and neither recess nor protrusion is provided in a surface thereof. As illustrated in FIG. 16(b), a support tube joining portion 414 of the camera unit has a through hole K which has a circular opening and a moat-shaped recess H which is formed as a moat surrounding the through hole K. As illustrated in FIG. 16(c), by thrusting the camera support tube 57 into the moat-shaped recess H in a state where the camera-side cable 12 is inserted into the through hole K of the support tube joining portion, the camera unit and the camera support tube 57 are joined by frictional contact.

In Embodiment 7, the camera support tube 57 is held between an inner peripheral wall and an outer peripheral of the moat-shaped recess H, so that joining strength of the camera unit and the camera support tube 57 is increased.

Embodiment 8

In Embodiment 1, the camera support tube is fixed to the cannula by the valve in the cannula, but there is no limitation thereto. FIG. 17(a) is a sectional view of a camera support tube of Embodiment 8, FIG. 17(b) is a sectional view of a cannula of Embodiment 8, and FIG. 17(c) is a sectional view illustrating a state where the camera support tube of (a), which is inserted into the cannula of (b), and the camera unit are joined. As illustrated in FIG. 17(a), a camera support tube 71 is a funnel-shaped tube and includes a head part in a conical shape and a leg part in a cylindrical shape, and the locking holes 123 are provided in the leg part. Moreover, as illustrated in FIG. 17(b), a cannula 131 is a simple tubular device (having no valve or the like inside thereof), one end part (extracorporeal side) of which is thicker than the other end part (intracorporeal side). By inserting the camera support tube 71 into the cannula 131 with a tip end of the leg part of the camera support tube 71 abutting on the one end part (extracorporeal side) of the cannula 131, the head part of the camera support tube 71 becomes in contact with the one end part (extracorporeal side) of the cannula 131 as illustrated in FIG. 17(c), and the camera support tube 71 is held by the cannula 131. Accordingly, the thicker end part of the camera support tube 71 is out of the body, so that there is no possibility that the camera support tube 71 falls out into the body. Further, by fitting the locking holes 123 of the camera support tube 71 to the locking pawls 23 of the camera unit 11, the camera unit 11 and the camera support tube 71 are joined with high mechanical strength. Note that, the surgeon is able to change the orientation of the camera unit 11 by rotating the camera support tube 71.

As illustrated in FIG. 18(a), a camera support tube 81 is also able to be provided with a stopper 77 which is movable in a vertical direction (an extending direction of the tube). The stopper 77 is to be moved by an operation of the surgeon, and is an elastic body such as rubber, into which the camera support tube 81 is inserted. Note that, the stopper 77 may be set to be movable also by setting the stopper 77 and the camera support tube 81 to have a screw structure. In this case, as illustrated in FIG. 18(b), by inserting the camera support tube 81 into the cannula 131, the stopper 77 of the camera support tube 81 abuts on an edge (extracorporeal side) of the cannula 131, and the camera support tube 81 is held by the cannula 131. In addition, by fitting the locking holes 123 of the camera support tube 81 to the locking pawls 23 of the camera unit 11, the camera unit 11 and the camera support tube 81 are joined with high mechanical strength. Note that, the surgeon is able to, for example, change a position of the camera unit 11 (zooming for imaging) by vertically moving the stopper 77 or change the orientation of the camera unit 11 by rotating the camera support tube 81.

Embodiment 9

In Embodiments 1 and 2, the locking holes (recesses) are provided in the side surface of the camera support tube and the locking pawls (protrusions) are provided in the side surface of the support tube joining portion, but it is possible to make a configuration such that not a structure in which the locking holes (recesses) and the locking pawls (protrusions) are provided in the side surface of the support tube in this manner but a structure in which a cylinder tip of the support tube has a corrugated uneven structure is included, and that an uneven structure corresponding to this uneven structure is provided in the joining portion.

FIG. 20(a) is a perspective view of a main part of a camera support tube of Embodiment 9, FIG. 20(b) is a sectional view of a main part of the camera support tube and a support tube joining portion of Embodiment 9, FIG. 20(c) is a sectional view illustrating a state where the camera support tube and the support tube joining portion in Embodiment 9 are joined, and FIG. 20(d) is a development view of a corrugated part of the camera support tube and the support tube joining portion.

As illustrated in FIG. 20(a), a camera support tube 94 is a cylindrical tube, and neither recess nor protrusion is provided in a side surface thereof, but an uneven structure 96 which is corrugated is provided in a cylinder tip. On the other hand, as illustrated in FIG. 20(b), a support tube joining portion 95 provided in the camera unit has a hollow structure whose opening is circular, and an uneven structure 196 which is corrugated is provided in an inner wall thereof. Note that, the uneven structures 96 and 196 only need to have a repeating pattern having two or more sets of a recess and a protrusion. Moreover, because of having a rounded shape, the uneven structure 96 in a tip end of the camera support tube 94 does not damage a human body even when erroneously being in contact therewith, and is therefore safe.

A tip end part of the camera support tube 94 has a tapered shape, and, in accordance therewith, the support tube joining portion 95 has an inner wall inclined and has a tapered shape whose hole diameter is small as being apart from the opening. Thereby, insertion of the camera support tube 94 into the support tube joining portion 95 is facilitated. In this case, the camera support tube 94 may have a tapered shape obtained by reducing thickness thereof. Furthermore, by setting an inner diameter of the camera support tube 94 to be fixed and changing only an outer diameter, when a tool is inserted into the cylinder, it is not likely to be hooked midway and becomes unable to be pulled out, so that it is more desirable.

Then, as illustrated in FIG. 20(c), by thrusting the camera support tube 94 into the support tube joining portion 95 and, after lightly butting thereagainst, thrusting the camera support tube 94 with light rotation, the uneven structure 96 of the camera support tube 94 engages with the uneven structure 196 of the support tube joining portion 95 as illustrated in the development view of FIG. 20(d), so that the camera support tube 94 is firmly joined to the camera unit.

Each of the corrugated uneven structures 96 and 196 has a structure in which tip end parts of the protrusions or bottom parts of the recesses slightly spread, and at least one of the uneven structure 96 of the camera support tube 94 and the uneven structure 196 of the support tube joining portion 95 is formed of an elastic material such as resin. Accordingly, the elastic material in the protrusions of the uneven structure 196 or the uneven structure 96 passes through slightly narrowed sites of the recesses of the uneven structure 96 or the uneven structure 196, while deforming, and, after passing through, returns to an original shape thereof with elastic force, and the uneven structure 96 and the uneven structure 196 are firmly fit. Thereby, there is an advantage that an impact of fitting (click feeling) is transmitted to a hand of the surgeon, and the surgeon is able to recognize that the fitting has been completed. Note that, in consideration for a heat radiation property or durability, an elastic material may be used only for deforming parts (for example, about the middle of the protrusions or the recesses) of the uneven structure 96 or the uneven structure 196.

Moreover, it is possible to form the camera support tube 94 with a hard material such as SUS and to form the side surface of the support tube joining portion 95 with an elastic material such as rubber. In this case, by thrusting the camera support tube 94 into the support tube joining portion 95, the camera support tube 94 is fastened with an elastic property of the support tube joining portion 95, and the camera unit and the camera support tube 94 are joined with high mechanical strength. However, since it is necessary to secure a heat radiation property, it is desirable to combine and use materials such as metal, which have excellent thermal conductivity (for example, use a metal material which has excellent thermal conductivity for tip ends of the protrusions and bottom parts of the recesses, and use an elastic material for the middle of the protrusions or the recesses).

Further, it is desirable to be formed by using a plurality of materials which have different characteristics, for example, by forming the side surface of the support tube joining portion 95 with a material which has excellent thermal conductivity (metal or the like) and using an elastic material for the uneven structure 196. Thereby, both of required properties such as a joining property and a heat radiation property are able to be achieved. Note that, regardless of the aforementioned formation examples, the materials may be combined in a reversed manner.

Furthermore, such a modified example of the support tube and the joining portion and the materials for components being able to be used in a plurality of combinations are also similarly applicable to Embodiment 1 to Embodiment 8.

[Overview]

An in-body monitoring camera system of an aspect 1 of the invention includes: a support tube one end part of which is introduced into a body;

an imaging portion which is joined to the support tube inside the body; a joining portion which joins the imaging portion and the support tube; a cable which is connected to the imaging portion and led out to an outside of the body through the support tube; and a control system that is provided outside the body is connected to the cable, and includes at least a display apparatus.

In an in-body monitoring camera system of an aspect 2 of the invention, the imaging portion includes at least one (for example, two) gripping portion in the in-body monitoring camera system of the aspect 1.

In an in-body monitoring camera system of an aspect 3 of the invention, at least a part of the joining portion and a part of the support tube is formed of an elastic material in the in-body monitoring camera system of the aspect 1 or 2.

In an in-body monitoring camera system of an aspect 4 of the invention, the joining portion has a recess shape corresponding to the one end part of the support tube, and a protrusion or a recess for mechanically fixing the end part of the support tube is provided in an inner wall of the joining portion, in the in-body monitoring camera system of the aspect 1 or 2.

In an in-body monitoring camera system of an aspect 5 of the invention, the protrusion is a locking pawl or a screw thread in the in-body monitoring camera system of the aspect 4.

In an in-body monitoring camera system of an aspect 6 of the invention, a part from which the cable is pulled out is provided in an inner part of the joining portion, and the cable is adhesively fixed to the inner part of the joining portion at the part, in the in-body monitoring camera system of the aspects 1 to 5.

In an in-body monitoring camera system of an aspect 7 of the invention, mechanical fixation of the support tube is performed by screwing the support tube in a first direction and the fixation is released by screwing the support tube in a second direction opposite to the first direction, in the in-body monitoring camera system of the aspects 1 to 6.

A support tube of an aspect 8 of the invention is the support tube of the in-body monitoring camera system according to the aspect 4, and includes a recess or a protrusion corresponding to a shape of the protrusion or the recess provided in the inner wall of the joining portion.

As to a support tube of an aspect 9 of the invention, the support tube has a shape an inner diameter of which is fixed and an outer diameter of which, in a part joining to the joining portion, becomes small as being close to a tip end thereof, in the support tube of the aspect 8.

In an in-body monitoring camera system of an aspect 10 of the invention, a sectional surface of the support tube has a circular shape or a square shape in the in-body monitoring camera system of any one of the aspects 1 to 5.

An in-body monitoring camera system of an aspect 11 of the invention includes a tubular structure capable of being inserted into a body wall, and further includes a holding tube for holding the support tube which is inserted into an inner part thereof, in the in-body monitoring camera system of any one of the aspects 1 to 7.

An installation method of an in-body monitoring camera of an aspect 12 of the invention includes: a step of introducing, into a body, an imaging portion and a cable connected to the imaging portion; a step of introducing a part of a support tube into the body; a step of inserting the cable into the support tube; and a step of, inside the body, joining the imaging portion and the support tube at a recess-shaped joining portion which is provided in the imaging portion.

In an installation method of an in-body monitoring camera of an aspect 13 of the invention, the step of joining the imaging portion and the support tube inside the body is performed with at least two sites of the imaging portion gripped inside the body with a surgical tool in the installation method of the in-body monitoring camera of the aspect 12.

In an installation method of an in-body monitoring camera of an aspect 14 of the invention, at the step of joining the imaging portion and the support tube inside the body, a recess provided in the support tube is fit to a protrusion provided in an inner wall of the joining portion by operating a part of the support tube, which is out of the body, in the installation method of the in-body monitoring camera of the aspect 12 or 13.

In an installation method of an in-body monitoring camera of an aspect 15 of the invention, at the step of introducing the part of the support tube into the body, by inserting the support tube into an inner part of a holding tube a part of which is inserted into the body, the part of the support tube is introduced into the body and the support tube is held by the holding tube, in the installation method of the in-body monitoring camera of any one of the aspects 12 to 14.

An imaging apparatus of an aspect 16 of the invention includes an imaging portion capable of being introduced into a body and a cable connected to the imaging portion, in which a joining portion which allows joining of a support tube one end part of which is introduced into the body and the imaging portion inside the body is provided in the imaging portion, and the cable is led out to an outside of the imaging portion through the joining portion.

An in-body monitoring camera system of an aspect 17 of the invention includes: a support tube one end part of which is introduced into a body; an imaging portion which is joined to the support tube inside the body; a joining portion which joins the imaging portion and the support tube; a first cable which is connected to the imaging portion and led out to an outside of the body through the support tube; and a control system that is provided outside the body is electrically connected to the first cable, and includes at least a display apparatus.

In an in-body monitoring camera system of an aspect 18 of the invention, a part from which the first cable is pulled out is provided in an inner part of the joining portion, and the first cable is adhesively fixed to the inner part of the joining portion at the part, in the in-body monitoring camera system of the aspect 17.

In an in-body monitoring camera system of an aspect 19 of the invention, at least a part of the joining portion and a part of the support tube is formed of an elastic material in the in-body monitoring camera system of the aspect 17 or 18.

In an in-body monitoring camera system of an aspect 20 of the invention, the joining portion has a recess shape corresponding to the one end part of the support tube, and a protrusion or a recess for mechanically fixing the end part of the support tube is provided in an inner wall of the joining portion, in the in-body monitoring camera system of any one of the aspects 17 to 19.

In an in-body monitoring camera system of an aspect 21 of the invention, the protrusion is a locking pawl in the in-body monitoring camera system of the aspect 20.

In an in-body monitoring camera system of an aspect 22 of the invention, mechanical fixation of the support tube is performed by screwing the support tube in a first direction and the fixation is released by screwing the support tube in a second direction opposite to the first direction, in the in-body monitoring camera system of the aspect 20.

In an in-body monitoring camera system of an aspect 23 of the invention, joining strength of the support tube and the joining portion is smaller than connection strength of the imaging portion and the first cable in the in-body monitoring camera system of any one of the aspects 17 to 22.

In an in-body monitoring camera system of an aspect 24 of the invention, the joining strength is in a range of 3 N to 6 N in the in-body monitoring camera system of the aspect 23.

In an in-body monitoring camera system of an aspect 25 of the invention, the protrusion is a screw thread in the in-body monitoring camera system of the aspect 20 or 22.

In an in-body monitoring camera system of an aspect 26 of the invention, a different cable electrically connected to the control system is further included, a first connector provided in the first cable is fit to a second connector provided in the different cable, and fitting strength of the first and the second connectors is smaller than connection strength of the imaging portion and the first cable, in the in-body monitoring camera system of any one of the aspects 17 to 25.

In an in-body monitoring camera system of an aspect 27 of the invention, the fitting strength is in a range of 4 N to 10 N in the in-body monitoring camera system of the aspect 26.

In an in-body monitoring camera system of an aspect 28 of the invention, a different cable electrically connected to the control system is further included, a first connector provided in the first cable is fit to a second connector provided in the different cable, and an outer diameter of the first connector is equal to or less than an outer diameter of the second connector, in the in-body monitoring camera system of any one of the aspects 17 to 27.

In an in-body monitoring camera system of an aspect 29 of the invention, a different cable electrically connected to the control system is further included, a first connector provided in the first cable is fit to a second connector provided in the different cable, the different cable has a clean part maintaining cleanliness, which is a part having a predetermined length from a position at which the first connector and the second connector are fit, and a value of a length of the first cable is a half of or less than a sum of the length of the first cable and the length of the clean part, in the in-body monitoring camera system of any one of the aspects 17 to 28.

In an in-body monitoring camera system of an aspect 30 of the invention, an outer diameter of the support tube at one end part is larger than an outer diameter of the support tube at the other end part that is to be fit to the joining portion, in the in-body monitoring camera system of any one of the aspects 17 to 29.

In an in-body monitoring camera system of an aspect 31 of the invention, a different cable electrically connected to the control system is further included, a first connector provided in the first cable is fit to a second connector provided in the different cable, and a part or entire of at least one of surfaces of the imaging portion, the first cable, and the first connector is colored blue or green, in the in-body monitoring camera system of any one of the aspects 17 to 30.

In an in-body monitoring camera system of an aspect 32 of the invention, a different cable electrically connected to the control system is further included, a first connector provided in the first cable is fit to a second connector provided in the different cable, and a light accumulating material or a reflective material is used for a part or entire of at least one of surfaces of the imaging portion, the first cable, and the first connector, in the in-body monitoring camera system of any one of the aspects 17 to 31.

In an in-body monitoring camera system of an aspect 33 of the invention, a different cable electrically connected to the control system is further included, a first connector provided in the first cable is fit to a second connector provided in the different cable, and an outer diameter of the first cable is smaller than an outer diameter of the different cable, in the in-body monitoring camera system of any one of the aspects 17 to 32.

An in-body monitoring camera system of an aspect 34 of the invention further includes a second cable connected to the control system and a third cable connecting the first and the second cables, in the in-body monitoring camera system of any one of the aspects 17 to 33.

In an in-body monitoring camera system of an aspect 35 of the invention, an outer diameter of the third cable is larger than an outer diameter of the first cable and smaller than an outer diameter of the second cable in the in-body monitoring camera system of the aspect 34.

An in-body monitoring camera system of an aspect 36 of the invention further includes a tubular structure capable of being inserted into a body wall and a holding tube for holding the support tube which is inserted into an inner part thereof, in the in-body monitoring camera system of any one of the aspects 17 to 35.

A support tube of an aspect 37 of the invention includes a recess or a protrusion corresponding to a shape of the protrusion or the recess provided in the inner wall of the joining portion, in the support tube of the in-body monitoring camera system of the aspect 20.

As to a support tube of an aspect 38 of the invention, the support tube has a shape an inner diameter of which is fixed and an outer diameter of which, in a part joining to the joining portion, becomes small as being close to a tip end thereof, in the support tube of the aspect 37.

The invention is not limited to the embodiments described above, and what is obtained by appropriately modifying the embodiments described above based on common technical knowledge or by combining them is included in embodiments of the invention.

INDUSTRIAL APPLICABILITY

The present imaging apparatus is suitable for endoscopic surgery and the like.

REFERENCE SIGNS LIST 1 in-body monitoring camera system
11 camera unit (imaging portion)
12 camera-side cable (first cable)
13, 35 camera support tube (support tube)
14 support tube joining portion (joining portion)
15a camera-side cable connector (first connector)
15b device-side cable connector (second connector)
16 device-side cable (second cable)
31 cannula (holding tube)
43 intermediate cable (third cable)

The invention claimed is:

1. An in-body monitoring camera system, comprising:
a support tube, one end part of which is able to be introduced into a body;
an imaging portion which is arranged to be joined to the support tube inside the body;
a joining portion which joins the imaging portion and the support tube;
a first cable which is connected to the imaging portion and able to be led out to an outside of the body through the support tube; and
a control system that is electrically connected to the first cable, and includes at least a display apparatus, wherein
the joining portion is a recess-shaped joining portion formed in the imaging portion, and
the support tube is joined to the imaging portion by being inserted into the recess-shaped joining portion.

2. The in-body monitoring camera system according to claim 1, wherein a part from which the first cable is pulled out is provided in an inner part of the joining portion, and the first cable is adhesively fixed to the inner part of the joining portion at the part.

3. The in-body monitoring camera system according to claim 1, wherein at least a part of the joining portion and a part of the support tube is formed of an elastic material.

4. The in-body monitoring camera system according to claim 1, wherein the joining portion has a recess shape corresponding to the one end part of the support tube, and a protrusion or a recess for mechanically fixing the end part of the support tube is provided in an inner wall of the joining portion.

5. The in-body monitoring camera system according to claim 4, wherein the protrusion is a locking pawl.

6. A support tube of the in-body monitoring camera system according to claim 4, comprising a recess or a protrusion corresponding to a shape of the protrusion or the recess provided in the inner wall of the joining portion.

7. The support tube according to claim 6, wherein the support tube has a shape an inner diameter of which is fixed and an outer diameter of which, in a part joining to the joining portion, becomes small as being close to a tip end thereof.

8. The in-body monitoring camera system according to claim 1, wherein joining strength of the support tube and the joining portion is smaller than connection strength of the imaging portion and the first cable.

9. The in-body monitoring camera system according to claim 8, wherein the joining strength is in a range of 3 N to 6 N.

10. The in-body monitoring camera system according to claim 1, further comprising a different cable electrically connected to the control system, wherein a first connector provided in the first cable is fit to a second connector provided in the different cable, and
fitting strength of the first and the second connectors is smaller than connection strength of the imaging portion and the first cable.

11. The in-body monitoring camera system according to claim 10, wherein the fitting strength is in a range of 4 N to 10 N.

12. The in-body monitoring camera system according to claim 1, further comprising
a different cable electrically connected to the control system, wherein a first connector provided in the first cable is fit to a second connector provided in the different cable, and
an outer diameter of the first connector is equal to or less than an outer diameter of the second connector.

13. The in-body monitoring camera system according to claim 1, further comprising
a different cable electrically connected to the control system, wherein a first connector provided in the first cable is fit to a second connector provided in the different cable,
the different cable has a clean part maintaining cleanliness, which is a part having a predetermined length from a position at which the first connector and the second connector are fit, and
a value of a length of the first cable is a half of or less than a sum of the length of the first cable and the length of the clean part.

14. The in-body monitoring camera system according to claim 1, wherein an outer diameter of the support tube at one end part is larger than an outer diameter of the support tube at the other end part that is to be fit to the joining portion.

15. The in-body monitoring camera system according to claim 1, further comprising
a different cable electrically connected to the control system, wherein a first connector provided in the first cable is fit to a second connector provided in the different cable, and
a part or entire of at least one of surfaces of the imaging portion, the first cable, and the first connector is colored blue or green.

16. The in-body monitoring camera system according to claim 1, further comprising
a different cable electrically connected to the control system, wherein a first connector provided in the first cable is fit to a second connector provided in the different cable, and
a light accumulating material or a reflective material is used for a part or entire of at least one of surfaces of the imaging portion, the first cable, and the first connector.

17. The in-body monitoring camera system according to claim 1, further comprising
a different cable electrically connected to the control system, wherein a first connector provided in the first cable is fit to a second connector provided in the different cable, and
an outer diameter of the first cable is smaller than an outer diameter of the different cable.

18. The in-body monitoring camera system according to claim 1, further comprising:
a second cable connected to the control system and
a third cable connecting the first and the second cables.

19. The in-body monitoring camera system according to claim 18, wherein an outer diameter of the third cable is larger than an outer diameter of the first cable and smaller than an outer diameter of the second cable.

20. The in-body monitoring camera system according to claim 1, further comprising
a tubular structure capable of being inserted into a body wall and
a holding tube for holding the support tube which is inserted into an inner part thereof.

21. An in-body monitoring camera system, comprising:
a support tube, one end part of which is able to be introduced into a body;
an imaging portion which is arranged to be joined to the support tube inside the body;
a joining portion which joins the imaging portion and the support tube;
a first cable which is connected to the imaging portion and able to be led out to an outside of the body through the support tube; and
a control system that is electrically connected to the first cable, and includes at least a display apparatus, wherein
the joining portion has a recess shape corresponding to the one end part of the support tube, and a protrusion or a recess for mechanically fixing the end part of the support tube is provided in an inner wall of the joining portion, and
the protrusion is a locking pawl.

* * * * *